(12) United States Patent
Lundberg

(10) Patent No.: US 8,884,002 B2
(45) Date of Patent: Nov. 11, 2014

(54) VISCOSITY CONTROL IN COMPOSITIONS COMPRISING PLANT FIBER MATERIALS

(75) Inventor: Brock Lundberg, Osseo, WI (US)

(73) Assignee: Fiberstar Bio-Ingredient Technologies, Inc., River Falls, WI (US)

( * ) Notice: Subject to any disclaimer, the term of this patent is extended or adjusted under 35 U.S.C. 154(b) by 608 days.

(21) Appl. No.: 12/958,118

(22) Filed: Dec. 1, 2010

(65) Prior Publication Data

US 2012/0142909 A1    Jun. 7, 2012

(51) Int. Cl.
*C08L 1/02* (2006.01)
*C12P 19/04* (2006.01)
*C08B 15/00* (2006.01)
*D21C 9/00* (2006.01)

(52) U.S. Cl.
CPC ........... *D21C 9/002* (2013.01); *C08B 15/00* (2013.01); *C12Y 301/01011* (2013.01); *C12P 19/04* (2013.01); *C08L 1/02* (2013.01); *C08L 2205/16* (2013.01)
USPC ........................................... 536/80; 536/124

(58) Field of Classification Search
CPC .......... D21C 6/002; C98B 15/00; C08L 1/02; C08L 2205/16; C12Y 19/04
USPC .................................................... 536/80, 124
See application file for complete search history.

(56) References Cited

U.S. PATENT DOCUMENTS

| | | | |
|---|---|---|---|
| 3,462,283 A | 8/1969 | Hjermstad et al. | |
| 4,232,049 A | 11/1980 | Blake | |
| 4,413,017 A | 11/1983 | Loader | |
| 4,957,599 A | 9/1990 | Chou et al. | |
| 5,059,654 A | 10/1991 | Hou et al. | |
| 5,342,636 A | 8/1994 | Bakshi et al. | |
| 5,766,662 A | 6/1998 | Inglett | |
| 5,912,407 A * | 6/1999 | Miller et al. | 8/139 |
| 5,964,983 A | 10/1999 | Dinand et al. | |
| 7,071,155 B2 | 7/2006 | Griese et al. | |
| 7,074,300 B2 | 7/2006 | Lundberg et al. | |
| 7,094,317 B2 | 8/2006 | Lundberg et al. | |
| 7,186,680 B2 | 3/2007 | Caswell et al. | |
| 2003/0116289 A1 | 6/2003 | Lundberg et al. | |
| 2004/0086626 A1 | 5/2004 | Lundberg et al. | |
| 2005/0074542 A1 | 4/2005 | Lundberg et al. | |
| 2005/0271790 A1 | 12/2005 | Aronson et al. | |
| 2005/0274469 A1 | 12/2005 | Lundberg et al. | |
| 2006/0210687 A1 | 9/2006 | Lundberg et al. | |
| 2008/0193590 A1 * | 8/2008 | Lundberg | 426/2 |
| 2010/0021988 A1 | 1/2010 | Kerovuo et al. | |

FOREIGN PATENT DOCUMENTS

JP       51149976 A  * 12/1976
JP    2001271266 A  * 10/2001

OTHER PUBLICATIONS

Miller et al (JP 2001271266—English Language Abstract), 2001.*
Miller et al (JP 2001271266—English Language Machine Translated Copy), 2001.*
Haard and Chism, "Characteristics of Edible Plant Tissues," 1996, Food Chemistry. pp. 944-1011; Ed. By Fennema. Marcel Dekker NY, NY.
Gu, L., R Ruan, P. Chen, W. Wilcke, P. Addis. 2001. Structure Function Relationships of Highly Refined Cellulose. Transactions of the ASAE. vol. 44(6): pp. 1707-1712.
Ang and Miller in Cereal Foods World, Multiple Functions of Powdered Cellulose as a Food Ingredient, vol. 36 (7): 558-564 (1991).
http://www.gmo-compass.org/eng/database/enzymes/82.cellulase.html.
http://www-saps.plantsci.cam.ac.uk/osmoweb/cellulase.htm.

* cited by examiner

*Primary Examiner* — Brandon Fetterolf
*Assistant Examiner* — Everett White
(74) *Attorney, Agent, or Firm* — Mark A. Litman & Associates, P.A.

(57) ABSTRACT

Pectinases, such as Pectinex™ Ultra SP-L (composed of the enzyme Polygatacturonase, a type of pectinase which is derived from *Aspergillus aculeatus*) or pectinmethylesterases were used to decrease or increase, respectively, the viscosity of fiber solutions, especially solutions with highly refined cellulosic thickeners, and particularly those made of highly refined cellulosic parenchyma cell wall fiber solutions. The enzyme can reduce the viscosity up to 95% or increase the viscosity 100 fold. At lower concentrations the enzyme requires up to a few days of reacting to reach the full reduction in viscosity. Pectinex™ Ultra SP-L has an optimum pH of 4.5-5 and a temperature optimum of 40° C. By controlling the viscosity available from the dried, treated highly refined cellulosic fiber compositions, tailored powder compositions can be provided that will provide precise viscosities when rehydrated in solutions at a constant concentration.

20 Claims, 6 Drawing Sheets

FIGURE 5
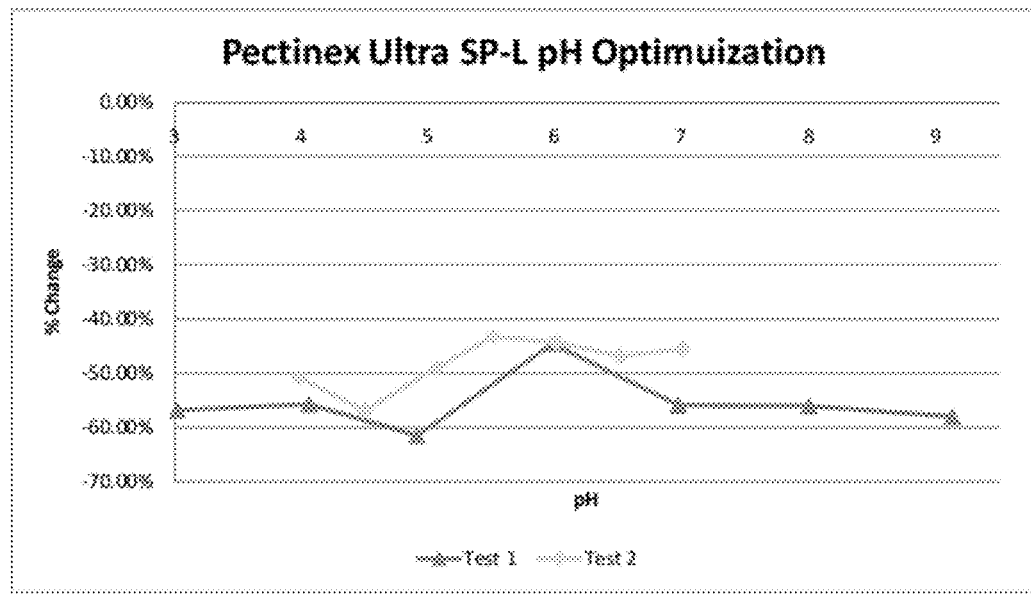
FIGURE 6 - The optimum temperature is 40 °C but well in a range of 30-50°C.
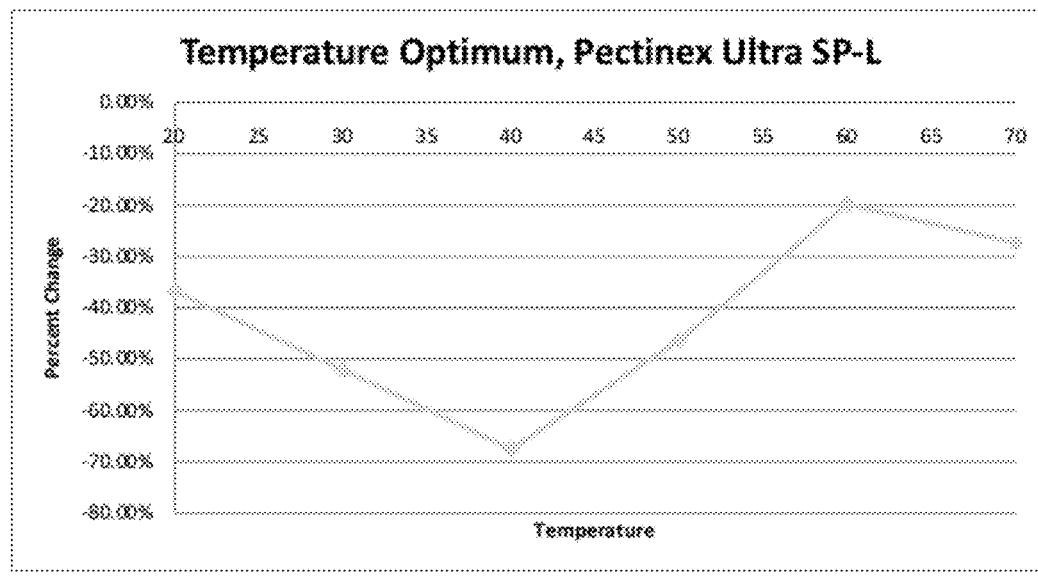

It appears that time trials are inconclusive for Pectinex Ultra SP-L.

VISCOSITY CONTROL IN COMPOSITIONS COMPRISING PLANT FIBER MATERIALS

BACKGROUND OF THE INVENTION

1. Field of the Invention

This invention relates to viscosity altering increasing compositions, and particularly plant fiber materials and highly refined cellulosic fibers (HRC fibers) by altering viscosity which have been treated with pectinase, cellulase, and/or pectinmethylesterase to modify the natural viscosity provided by fibers, and especially those fibers produced from plant mass and especially HRC fiber mass.

2. Background of the Art

Highly refined cellulose materials (HRC materials) are well known in the literature and are disclosed, for example, in U.S. patent application Ser. No. 11/440,603, filed May 25, 2006, which is in turn a continuation-in-part of U.S. patent application Ser. No. 11/165,430, filed Jun. 30, 2005, titled "REDUCED FAT SHORTENING, ROLL-IN, AND SPREADS USING CITRUS FIBER INGREDIENTS," which is a continuation-in-part of U.S. patent application Ser. No. 10/969,805, filed 20 Oct. 2004, and titled "HIGHLY REFINED CELLULOSIC MATERIALS COMBINED WITH HYDROCOLLOIDS," which is a continuation-in-part of U.S. patent application Ser. No. 10/288,793, filed Nov. 6, 2002, titled "HIGHLY REFINED FIBER MASS, PROCESS OF THEIR MANUFACTURE AND PRODUCTS CONTAINING THE FIBERS."

U.S. Pat. No. 5,059,654 (Hou et al.) describes affinity matrices for supports, including refined cellulose fiber supports forming enzymatic supports with linking moieties (e.g., aldehydes).

Materials and compositions that alter, and especially increase the viscosity of liquid compositions are referred to in the art by various names such as thickening agents, any variety of generally hydrophilic materials which, when incorporated in the compositions described herein, may act as viscosity modifying agents, emulsifying and/or solubilizing agents, suspending agents, and tonicity raising agents. It is contemplated that the thickening agents or viscofying agents may be capable of aiding in maintaining the stability of the compositions due to such properties. These agents may be inorganic (e.g., clays, silicas, metal oxides) or organic (polymers, corn starch, fatty acids, gelatin, carbohydrates, and the like) or mixtures thereof. Other specific examples include carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000, and polysiloxanes, especially poly dialkoxy-silanes with weight average molecuylar weights between 500 and 100,000. The control of viscosity is usually a direct function of the amount of the viscosity modifying agent added to the composition. Some viscosity modifying agents are even responsive to the amount of shear force applied to the solution or dispersion (e.g., thixotropic agents).

U.S. Pat. No. 7,186,680 (Caswell et al.), "Laundry System Having Unitized Dosage" describes shape retention polymers useful in detergents that are transferred to fabrics. These shape retention additives are described in detail with examples of natural shape retention polymers are starches and their derivatives, and chitins and their derivatives. Starch is not normally preferred, since it makes the fabric resistant to deformation. However, it does provide increased "body" which is often desired. Starch is particularly preferred however, when the consumer intends to iron the fabrics after they have been washed and dried. When used, starch may be used as a solid or solubilized or dispersed to be combined with other materials in the composition. Any type of starch, e.g. those derived from corn, wheat, rice, grain sorghum, waxy grain sorghum, waxy maize or tapioca, or mixtures thereof and water soluble or dispersible modifications or derivatives thereof, can be used in the compositions of the present invention. Modified starches may include natural starches that have been degraded to obtain a lower viscosity by acidic, oxidative or enzymatic depolymerization. Additionally, low viscosity commercially available propoxylated and/or ethoxylated starches are useable in the present composition and are preferred when the composition is to be dispensed with a sprayer because of their low viscosity at relatively high solid concentrations. Suitable alkoxylated, low viscosity starches are sub-micron-size particles of hydrophobic starch that are readily dispersed in water and are prepared by alkoxylation of granular starch with a monofunctional alkoxylating agent which provides the starch with ether linked hydrophilic groups. A suitable method for their preparation is taught in U.S. Pat. No. 3,462,283.

U.S. Pat. No. 7,071,155 (Griese et al.) describes non-polymer thickening agents for cleaning compositions.

All references cited in this document are incorporated in their entirety by reference.

SUMMARY OF THE INVENTION

Refined cellulose fibers, processed cellulose fibers and other plant materials can increase the viscosity of aqueous liquids, suspensions, dispersions or solutions when added in an amount of at least 1% by total weight of the aqueous liquid or solution are treated with an enzyme to alter the viscosity modifying properties of the refined cellulose particles or fibers. The treatment of plant fibers and/or highly refined cellulose materials with pectinase, cellulase, and/or pectinmethylesterase enzymes and combinations thereof is particularly desirable.

Pectinases, such as Pectinex™ Ultra SP-L (composed of the enzyme Polygatacturonase, a type of pectinase which is derived from *Aspergillus aculeatus*) may be used to decrease the viscosity of refined cellulose fiber thickening agents, especially highly refined cellulose fiber thickening agents, and most particularly citric fiber highly refined cellulose solutions/dispersions/suspensions, especially solutions with highly refined cellulosic thickeners, and particularly those made of highly refined cellulosic orange fiber solution. The enzyme can reduce the viscosity up to 95% of the viscosity provided by untreated highly refined cellulose fiber compositions. At lower concentrations the enzyme requires up to a few days of reacting to reach the full reduction in viscosity. Pectinex™ Ultra SP-L has an optimum pH of 4.5-5 and a temperature optimum of 40° C. By controlling the viscosity available from the dried, treated highly refined cellulosic fiber compositions, tailored powder compositions can be provided that will provide precise viscosities when rehydrated in solutions at a constant concentration.

Pectinmethylesterases are another class of enzymes that modify the pectin structure in plant materials. These enzymes modify the pectin structure by pectin structure are associated with changing in cellular adhesion, plasticity, pH and ionic contents of the cell wall. They can make plant materials to thicken or even gel.

Another enzyme used in this invention is a class of enzymes called cellulases. By cleaving cellulose molecules, cellulose enzymes reduce the molecular weight of cellulose thereby changing their water holding and viscosity properties.

BRIEF DESCRIPTION OF THE FIGURES

FIG. 5 shows graphing of properties of treated materials according to the present technology.
FIG. 6 shows graphing of properties of treated materials according to the present technology.

DETAILED DESCRIPTION OF INVENTION AND PREFERRED EMBODIMENTS

Figure 1:
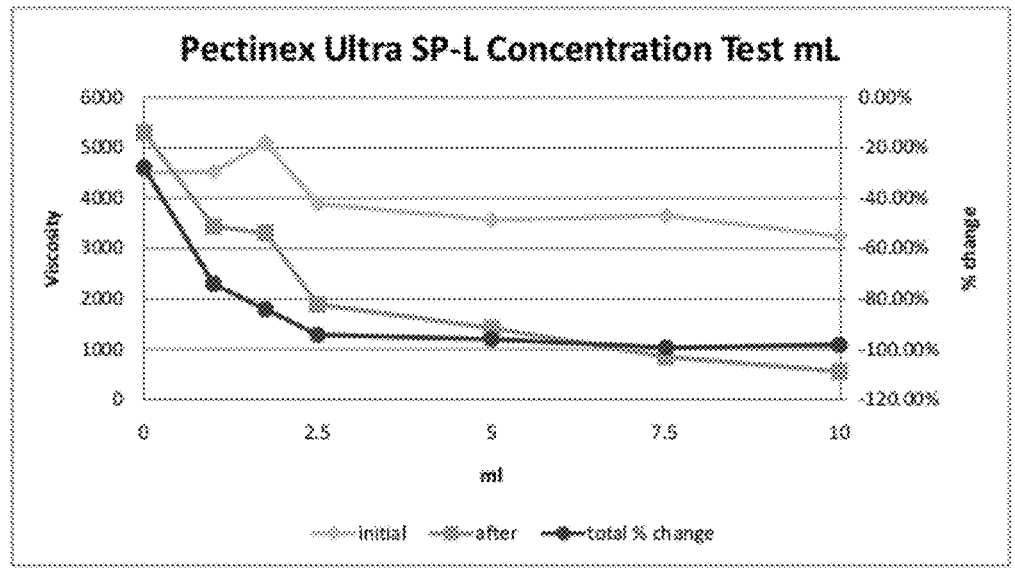
FIG. 1 shows graphing of properties of treated materials according to the present technology.

1. The present technology includes a dry refined cellulose composition having an enzymatically-modified cellulose fiber, cellulose powder, cellulose particles, refined cellulose fiber or refined cellulose particle, the enzymatic modification of the refined cellulose fiber reduces or increases the viscosity and enhance the properties of the refined cellulose fiber or refined cellulose particle before modification. The dry composition may have the refined cellulose fiber or refined cellulose particle before after enzymatic modification has a total dietary fiber (TDF) content greater than 30% as measured by AOAC 991.43 and comprises less than 90% soluble fiber. The refined cellulose fiber or refined cellulose particle may come from any plant material or be from citrus mass such as orange mass, lemon mass, lime mass, etc. The composition may have an enzyme used to modify the refined cellulose fiber or refined cellulose particle that is a pectinase, pectinmethylesterases, or cellulose enzymes. The dry composition has a property of increasing viscosity of deionized water by at least 10 centipoise at 25° C. at a weight-to-weight ratio of 0.1/1 for the reduced viscosity treatment and at least 1000 centipoise at 25° C. at a weight-to-weight ratio of 0.1/1, enzymatically-modified refined cellulose/deionized water, while the refined cellulose fiber or refined cellulose particle before enzymatic-modification has a property of increasing viscosity of deionized water by 500 plus 10% centipoise at 25° C. at a weight-to-weight ratio of 0.1/1, refined cellulose/deionized water. "Enzymatic-modification" means treating the fiber with an enzyme that chemically alters the plant mass and resulting in a change in viscosity under the test procedures described herein for measurement of viscosity. For example, comparing viscosity for the property of increasing viscosity of deionized water by at least 50 centipoise at 25° C. at a weight-to-weight ratio of 0.1/1, enzymatically-modified refined cellulose/deionized water, while the refined cellulose fiber or refined cellulose particle before enzymatic-modification has a property of increasing viscosity of deionized water by the at least 50 centipoise plus 20% centipoise at 25° C. at a weight-to-weight ratio of 0.1/1, refined cellulose/deionized water.

Also described is a method of reducing viscosity-increasing effects of a refined cellulose fiber in which there may be steps of:
  providing an aqueous volume;
  adding to the aqueous volume from 0.5% to 10% by weight of refined cellulose fiber to form a first reagent composition;
  adding from 0.25% to 8% by volume pectinase, cellulase, and/or pectinmethylesterases to the first reagent composition at a temperature of from 20° C. to 80° C.;
  allowing the pectinase, cellulase, and/or pectinmethylesterases to modify the refined cellulose fiber or particle (preferably modifying chemical structure of the cellulose fiber and/or additional chemistry carried by the cellulose fiber/particle, such as lignin or sugars, such modification including, but not limited to, hydrolysis, esterification, etherification, dimerization, increasing ionic strength of available groups, and the like) for at least 15 minutes to form a final liquid composition; and
  removing the modified refined cellulose from the final liquid composition.

The refined cellulose may be present as from 2% by weight to 8% by weight in the first reagent composition. The temperature may preferably be maintained between 30° C. and 50° C. or 30° C. to 60° C. for between 30 minutes and three hours before removing the modified refined cellulose. The refined cellulose in the method preferably is highly refined cellulose having a total dietary fiber (TDF) content greater than 30% as measured by AOAC 991.43 and a water holding capacity greater than five parts water per part fiber as measured by AACC 56-30 and comprises less than 90% soluble fiber. In the method, pH in the first reagent composition preferably is maintained between 3.0 and 9.0 during conversion to the final liquid composition and the refined cellulose is present as from 2% by weight to 8% by weight in the first reagent composition and the temperature in the first reagent composition is maintained between 30° C. and 65° C.

A liquid aqueous solution/dispersion/suspension contains a refined cellulose in which at least some of the refined cellulose has been treated with an enzyme to lower its viscosity-increasing properties in the aqueous liquid. In particular, refined cellulose fibers or particles that increase the viscosity of aqueous liquids or solutions when added in an amount of at least 1% by total weight of the aqueous liquid or solution are treated with an enzyme to alter the viscosity modifying properties of the refined cellulose particles or fibers. The treatment of highly refined cellulose materials with pectinase enzymes is particularly desirable.

Pectinases, such as Pectinex™ Ultra SP-L (composed of the enzyme Polygatacturonase, a type of pectinase which is derived from *Aspergillus aculeatus*) may be used to decrease the viscosity of refined cellulose fiber thickening agents, especially highly refined cellulose fiber thickening agents, and most particularly citric fiber highly refined cellulose solutions/dispersions/suspensions, especially solutions with highly refined cellulosic thickeners, and particularly those made of highly refined cellulosic orange fiber solution. The enzyme can reduce the viscosity up to 95% of the viscosity provided by untreated highly refined cellulose fiber compositions. At lower concentrations the enzyme requires up to a few days of reacting to reach the full reduction in viscosity. Pectinex™ Ultra SP-L has an optimum pH of 4.5-5 and a temperature optimum of 40° C. By controlling the viscosity available from the dried, treated highly refined cellulosic fiber compositions, tailored powder compositions can be provided that will provide precise viscosities when rehydrated in solutions at a constant concentration.

Pectinmethylesterases (PME) modify the pectin structure in plant materials. These enzymes modify the pectin structure by pectin structure are associated with changing in cellular adhesion, plasticity, pH and ionic contents of the cell wall. They can make plant materials thicken or even gel. Therefore, by modifying the structure of the plant cells (the molecular structure of some compounds in the cells, the cell walls, or carried by the cells) and specifically chemically modifying pectin within the cellulose plant mass and/or cells, PME can significantly modify the functional properties of plant materials. At least some of these changes should cause a specific concentration of plant cell material (e.g., cellulose fibers, cellulose particles, pulp, plant particles, fiber particles and the like). Because pectin represents up to 30% of polysaccharides in dicotyledonous plants, pectin plays a significant role in the functionality of plant materials. The main pectin component is homogalacturonan, consisting of a-Dgalacturonic acid residues linked by a a-1,4 glycosidic bond. The chemical groups consist of carboxyl groups and galacturonic acid residues, which can be methylesterified and the degree of methylesterification depends on the type of cell. The number and free and unesterified galacturonate carboxyl groups along the pectin chain influence the pectin properties and the cell wall firmness. PME regulates the number and distribution of free carboxyl groups along the pectin molecule.

Another enzyme used in this invention is a class of enzymes called cellulases. By cleaving cellulose molecules, cellulose enzymes reduce the molecular weight of cellulose thereby changing their water holding and viscosity properties. There are several different types of cellulases and their mechanisms vary. For instance, the cellulose can cleave cellulose molecules at the center of molecular chain and leaves shorter but still relatively long cellulose chains remaining. These types of cellulase enzymes are generally consider endoglucanases. Another type of cellulase enzymes cleave the end units of the cellulose chain and leave short disaccharides or even monosaccharides. These types of cellulases are considered either exocellulases or cellobioase enzymes.

Cellulases contribute to the enzymatic splitting of cellulose. They are used as reinforcing material in all plant tissues, cellulose is the most widespread organic compound in terms of quantity. It commonly may be found together with other structural substances such as ɛ lignin or hemicellulose. Cellulose cannot be exploited in the human digestive tract using the body's own emzymes. Cellulose is broken down by microbial flora present in the large intestine, but the resulting products are not absorbed by the body. In nutrition, cellulose is regarded as roughage.

Cellulases are reported to be used in some technical processes to make soluble the cellulose that is present in plant-based raw materials. It is counterintuitive, therefore, that cellulose can be used in a treatment process of cellulose and plant cell materials to break down cell or fiber chemical structure to increase the viscosity of compositions containing the cellulose-treated plant materials.

Any aqueous-based or aqueous-containing liquid or flowable aqueous composition (creams, gels, and the like) may comprises 0.005%-5% by total weight of a fiber material that has a total dietary fiber (TDF) content greater than 30% as measured by AOAC 991.43 and a water holding capacity greater than five parts water per part fiber as measured by AACC 56-30 and comprises less than 90% soluble fiber that has been enzymatically modified according to the teachings of the present technology.

An aqueous or liquid product may also comprise 0.005%-5% (e.g., 0.010-4%, 0.05-4%, 0.80-3%, and 0.05-5%) by total weight in the final product, including enzymatically-modified viscosity-increasing composition of a refined cellulosic fiber material that originally had a total dietary fiber (TDF) content greater than 30% as measured by AOAC 991.43 and a water holding capacity greater than five parts water per part fiber as measured by AACC 56-30 and comprises less than 90% soluble fiber where all or a portion of the milk solids are reduced (e.g., less than 5% by total weight, less than 4% by total weight, less than 3% by total weight, less than 2% by total weight, less than 1% by total weight to 0% by total weight) using the fiber material.

Another enzymatically-modified viscosity-increasing composition of a refined cellulosic fiber material product may comprise 0.05%-5% by total weight of a fiber material that originally had a total dietary fiber (TDF) content greater than 30% as measured by AOAC 991.43 and a water holding capacity greater than five parts water per part fiber as measured by AACC 56-30 and comprises less than 90% soluble fiber where all or a portion of the carageenan products are reduced (e.g., less than 5% by total weight, less than 4% by total weight, less than 3% by total weight, less than 2% by total weight, less than 1% by total weight to 0% by total weight) using the fiber material.

A liquid or aqueous product comprising 0.05%-5% by total weight of a fiber material comprising enzymatically-modified viscosity-increasing composition of a refined cellulosic fiber material that originally had a total dietary fiber (TDF) content greater than 30% as measured by AOAC 991.43 and a water holding capacity greater than five parts water per part fiber as measured by AACC 56-30 and comprises less than 90% soluble fiber where all or a portion of the gums and other water binders in the meat are reduced (e.g., less than 5% by total weight, less than 4% by total weight, less than 3% by total weight, less than 2% by total weight, less than 1% by total weight to 0% by total weight) using the fiber material.

A highly refined cellulose material is a composition of matter is defined in variously in the art by way of its properties. For example, copending U.S. patent application Ser. No. 10/303,256 describes HRC fibers as cellulosic mass from organic mass derived from agricultural plants comprising a highly refined cellulose (HRC) having a lignin concentration of at least 1% by weight and a water retention capacity of at least about 20 g $H_2O$/g dry HRC, possibly an oil retention capacity of at least about 10 g/g dry HRC, and possibly further having an oil retention capacity of at least about 10 g/g dry HRC and or a Langmuir surface area of at least about 7 $m^2$/g. The HRC may have an average pore diameter of at least about 5 angstroms and may have a Langmuir surface area of at least about 7 $m^2$/g. That reference is incorporated herein in its entirety.

HRC material may alternatively be described as a fiber material that has a total dietary fiber (TDF) content greater than 30% as measured by AOAC 991.43 and a water holding capacity greater than five parts water per part fiber as measured by AACC 56-30 followed literally or with modifications as listed in the specifications and is less than 90% soluble fiber.

The HRC may, according to the practices of the technology described herein, be used as an ingredient in the preparation of non-leavened or leavened, vegetarian or meat-containing product that is prepared by baking, frying, broiling or other heated-prepared methods, the precooked mass comprising 0.05%-5.0% by weight of highly refined cellulose fiber or 0.01%-10% by total weight of the food product of the fiber gum combination. The combination of the fiber and gum is preferably made in advance of the mixture of the fiber/gum composition to the food product, which in part explains the relatively wide range of weight additions of these materials that is possible. When the fiber and gum materials are pre-combined, in the 5-50% range described above, preferably in a solution, they may affect the viscosity.

Highly refined cellulose fibers may be produced with a wide range of properties and by various distinct processes. For the purpose of this patent application we are defining highly refined cellulose fibers as those with a total dietary fiber (TDF) content greater than 30% as measured by AOAC 991.43 and a water holding capacity (WHC) greater than five parts water per part fiber as measured by AACC 56-30 followed literally or with the following modifications; namely, 1) using shearing to hydrate the fiber mass, and/or 2) only using the first stage steps (1-4) of AACC 56-30 to find the approximate WHC and using this as the final WHC value, and/or 3) determining the final or approximate WHC value at 2-10% solids instead of 10% or using 2.5 g of fiber mass for the sample size instead of 5 g as the procedure calls for. The varying products can produce highly refined cellulose products with a wide range of properties that are based in part upon both on the starting organic mass containing fibers and the process steps, parameters and reagents. The underlying objective of the various processes is to take fibrous and or cellular mass (usually from agricultural products, especially flora (plants), and to reduce the structure in maximum ways. For example, as the original mass is sheared, shredded, exploded, disrupted or otherwise reduced from a complete cellular structure to fibrils, fibers, particles and other structures that form parts of the original organic mass. Various references that teach such processes and resulting expanded, highly refined cellulose materials include but are not limited to U.S. Pat. Nos. 5,766,662; 5,342,636; 4,957,599; and copending U.S. patent application Ser. No. 10/969,805, filed 20 Oct. 2004, "HIGHLY REFINED CELLULOSIC MATERIALS COMBINED WITH HYDROCOLLOIDS," which is a continuation-in-part of U.S. patent application Ser. No. 10/288,793, filed Nov. 6, 2002, titled "HIGHLY REFINED FIBER MASS, PROCESS OF THEIR MANUFACTURE AND PRODUCTS CONTAINING THE FIBERS."

It is important to note the difference in the practice of the present technology of the term "highly refined cellulose" product as compared to the more conventional material referred to as "dietary fiber." Many teachings of baked products including cracker products include the use of dietary fiber as one method of improving dietary or nutritional benefits in the baked good. Dietary fiber generally refers to the use of bulk fiber material, usually in its less processed state (e.g., dried but not highly sheared) so that the fiber remains substantially intact and even cell wall structure and cell morphology can be readily seen under microscopic examination (e.g., 40× to 500× examination).

Published U.S. Patent Applications Nos. 20050274469; 20050271790; 20050074542; 20040086626; and 20030116289 disclose highly refined cellulose materials.

Prior art results according to the Chen patents were WRC values were measured for both the aqueous HRC gel and dried HRC powder using a process that used NaOH concentrations ranging from about 0.004 to 0.025 g NaOH/g water. The WRC values for both the HRC gel and HRC powder were in the range of about 20 to at least about 56 g $H_2O$/g dry HRC, depending on the concentration of the alkaline solutions as measured by AACC 56-10 at varying solids content, which were typically less than 5% and most commonly at 1%. Maximum WRC values for the gel of at least about 56 g $H_2O$/g dry HRC were obtained with a NaOH concentration of about 0.007 g NaOH/g $H_2O$. Drying the HRC gel resulted in a reduction of about three (3) to 15% in WRC, which may be attributed to structural damages such as recrystallization caused by dehydration. However, the HRC powder also exhibited high WRC values, having a maximum WRC value of at least about 56 g $H_2O$/g dry HRC at a NaOH concentration of about 0.007 g NaOH/g $H_2O$. Compared with WRC values for even earlier prior art HRC products of 3.5 to 10 g water/g dry powdered cellulose reported by Ang and Miller in Cereal Foods World, Multiple Functions of Powdered Cellulose as a Food Ingredient, Vol. 36 (7): 558-564 (1991), it was shown that both the HRC gel and powder of the Chen Patents had a much higher water-holding capacity than prior art materials known at the time of the invention.

Determination of Water-Retention Capacity (WRC) and Oil-Retention Capacity (ORC) WRC is a measure of the amount of water retained under standard centrifuge. The WRC values for both aqueous HRC gel and freeze-dried HRC were determined in accordance with Method 56-10 of the American Association of Cereal Chemists (AACC), except the water holding capacities were measured in a 1% hydrated state. In the ORC (oil retention capacity) test, the same procedure was used except oil was used instead of water.

Determination of Pore Size and Microsurface Area Both the pore size and the microsurface area of freeze-dried HRC samples were measured using a Micromeritics™ 2000 from Micromeritice Instrument Co. The test sample was weighed with a precision of 0.0001 g. In all cases, the test sample weight was more than 100 mg to reduce the effect of weighing errors. At 85° C. and 6 mmHg vacuum, the sample was degassed, and moisture and other contaminants were removed. The degassed sample was analyzed in a nitrogen gas environment. Average pore diameter, BET surface area and Langmuir surface area were measured. The BET surface area values were determined by calculating the monolayer volume of adsorbed gas from the isotherm data. The Langmuir surface area values were obtained by relating the surface area to the volume of gas adsorbed as a monolayer.

Results and Discussion—Pore Size and Surface Area

Average pore size is a measure of openness of the HRC structure. The average pore size increased rapidly as NaOH concentration was increased to 0.007%, then slowly with further increase in NaOH concentration. The surface area reached a maximum value at 0.007% NaOH, which also coincides with the maximum WRC discussed above. The decrease in surface area after the maximum value seems to suggest an increase in the ratio of large pores to small pores, which may contribute to the decrease in total surface area. In one embodiment, the processes of the Lundberg Application removes lignin to a sufficient degree or substantially inactivates it such that undesirable fiber clumping does not occur There is not a large apparent difference in terms of WHC/viscosity between the two products (the Chen product and the product of the Lundberg Application) in a wet form, but there is a significant and commercially and technically important difference between the products/processes is that 1) Chen never provided a method for drying the gel product or 2) rehydrating the dry product. Additionally, 3) the present process for citrus has no required chemical treatment and does not need any mechanical treatments to produce a dry product that rehydrates to a high WHC/viscosity gel. Additionally, there is less concern about all the surface area, and pore size measurements.

It is desired that the highly refined cellulose fiber materials used in the practice of the present technology have the following properties. The HRC materials should provide a viscosity of at least 200 cps (preferably at least 300 cps) at 20 C. in a concentration of 3% in deionized water after mild stifling for 4 hours, a water retention capacity of at least 8× the dry weight of fiber (preferably at least 10×, at least 15× and at least 20×), which may also be determined by filtering saturated fiber mass, draining excess water (e.g., under mild pressure of 50 g/10 cm² for three minutes), weighing the drained wet fiber mass, then dehydrating the drained mass (to less than 5% water retention/weight of the fiber) and weighing the dried product to determine the amount of absorbed water removed. This latter method is less preferred, but can address the issue that drying of fibers often changes their physical properties, and particularly dried fibers (unless additionally sheared) often lose WRC after drying.

A highly refined cellulosic material (e.g., cellulose, modified celluloses, derivatized celluloses, hemicellulose, lignin, etc.) product can be prepared by generally moderate treatment and still provide properties that are equivalent to or improved upon the properties of the best highly refined cellulose products produced from more intense and environmentally unfriendly processes. Fruit or vegetable cells with an exclusively parenchymal cell wall structure can be treated with a generally mild process to form highly absorbent microfibers. Cells from citrus fruit and sugar beets are particularly available in large volumes to allow volume processing to generate highly refined cellulose fibers with both unique and improved properties. These exclusively parenchymal microfibers (hereinafter referred to as EPM's) have improved moisture retention and thickening properties that enable the fibers to provide unique benefits when combined into edible products (e.g., baked goods, liquefied foods, whipped foods, meats, meat fillers, dairy products, yogurt, frozen food entrees, ice cream, etc.) and in mixtures that can be used to generate edible food products (e.g., baking ingredients, dehydrated or low hydration products).

A new process for making HRC cellulose from parenchyma cell wall products, e.g. citrus fruit and sugar beets by-products, is performed in the absence of a hydroxide soaking step. This is a significant advance over the prior art as described by the Chen and Lundberg patents. Dinand, et al. (U.S. Pat. No. 5,964,983) also recommends the use of a chemical treatment step in addition to bleaching. In the present invention we are able to attain higher functionality (measured as viscosity) compared to Dinand et al. even though we use less chemical treatment, which is likely due to the higher amount of shear and chemical energy we put into the materials. The product is able to display the same or improved water retention properties and physical properties of the more strenuously refined agricultural products of the prior art, and in some cases can provide even higher water retention values, thickening and other properties that can produce unique benefits in particular fields of use.

General descriptions of the invention include a highly refined cellulose product comprising microfibers derived from organic fiber plant mass comprising at least 50% by weight of all fiber mass as parenchymal fiber mass, the highly refined cellulose product having an alkaline water retention capacity of at least about 25 g $H_2O$/g dry highly refined cellulose product and methods for providing and using these products. The highly refined cellulose product may have a water retention capacity of at least 50 g $H_2O$/g dry highly refined cellulose product.

Parenchymal cell walls refer to the soft or succulent tissue, which is the most abundant cell wall type in edible plants. For instance, in sugar beets, the parenchyma cells are the most abundant tissue the surrounds the secondary vascular tissues (xylem and phloem). Parenchymal cell walls contain relatively thin cell walls compared to secondary cell walls are tied together by pectin (Haard and Chism, 1996, Food Chemistry. Ed. By Fennema. Marcel Dekker N.Y., NY) In secondary cell walls (xylem and phloem tissues), the cell walls are much thicker than parenchymal cells and are linked together with lignin (Smook). This terminology is well understood in the art.

As used in the practice of the present invention, the term "dry" or "dry product" refers to a mass that contains less than 15% by weight of fibers as water.

The organic fiber mass comprises at least 50% by weight of fiber mass from organic products selected from the group consisting of sugar beets, citrus fruit, grapes, tomatoes, chicory, potatoes, pineapple, apple, carrots and cranberries. A food product or food additive may have at least 0.05 percent by weight solids in the food product or food additive of the above described highly refined cellulose product. The food product may also have at least about one percent or at least about two percent by weight of the highly refined cellulosic fiber of the invention.

A method for refining cellulosic material may comprise:
soaking raw material from organic fiber plant mass comprising at least 50% by weight of all fiber mass as parenchymal fiber mass in an aqueous solution with less than 1% NaOH;

draining the raw material and allowing the raw material to sit for a sufficient period under conditions (including ambient conditions of room temperature and pressure as well as accelerated conditions) so that the fibers and cells are softened so that shearing can open up the fibers to at least 40%, at least 50%, at least 60%, or at least 70, 80, 90 or 95% of their theoretic potential. This will usually require more that 4 hours soaking to attain this range of their theoretic potential. It is preferred that this soaking is for more than 5 hours, and preferably for at least about 6 hours. This soaking time is critical to get the materials to fully soften. When such a low alkaline concentration is used in the soaking, without the set time, the materials do not completely soften and can not be sheared/opened up to their full potential. This process produces soaked raw materials; and the process continues with refining the soaked raw material to produce refined material; and drying the soaked raw material.

The process may perform drying by many different commercial methods, although some display improved performance in the practice of the present invention. It is preferred that drying is performed, at least in part, by fluid bed drying or flash drying or a combination of the two. An alternative drying process or another associated drying step is performed at least in part by tray drying. For example, fluid bed drying may be performed by adding a first stream of organic fiber plant mass and a second stream of organic fiber plant mass into the drier, the first stream having a moisture content that is at least 10% less than the moisture content of the second stream or organic fiber plant mass. The use of greater differences in moisture content (e.g., at least 15%, at least 20%, at least 25%, at least 40%, at least 50% weight-to-weight water percent or weight-to-weight water-to-solid percent) is also within the scope of practice of the invention. In the drying method, the water may be extracted with an organic solvent prior to drying. In the two stream drying process, the second stream of organic fiber plant mass may have at least 25% water to solids content and the first stream may have less than 15% water to solids content. These processes may be practiced as batch or continuous processes. The method may use chopping and washing of the cellulose mass prior to soaking.

Another description of a useful process according to the invention may include draining and washing the soaked raw material in wash water to produce washed material; bleaching the washed material in hydrogen peroxide to produce a bleached material; and washing and filtering the bleached material to produce a filtered material.

The drying of an expanded fiber material according to the invention may use room temperature or higher air temperatures that dry the expanded fiber product and maintain the fiber material's functionalities of at least two characteristics of surface area, hydrogen bonding, water holding capacity and viscosity. It is also useful to use backmixing or evaporating to bring the organic fiber plant mass to a solids/water ratio that will fluidize in air in a fluid bed air dryer. This can be particularly performed with a method that uses a fluid bed dryer or flash dryer to dry the expanded or highly refined cellulosic fiber product.

The use of a flash or fluid bed dryer is an advantage over the drying methods suggested by Dinand et al. We have found that through the use of a fluid bed or flash dryer, low temperatures and controlled humidity are not needed to dry the materials of the present invention. In fact, although nearly any drying temperature in the fluid bed or flash dryer can be used, we have dried the product of the present invention using high air temperatures (400 F.) and attained a dry product with near equivalent functional properties after rehydration compared to the materials before drying. Additionally, using the process of the present invention, any surface area expanded cellulosic product can be dried and a functional product obtained and is not limited to parenchyma cell wall materials. The use of a fluid bed or flash dryer, the use of relatively high drying air temperatures (400 F.+), and the ability to dry non parenchyma cell wall (secondary cell) and obtain a functional product is in great contrast to the relatively low temperatures, e.g. 100 C. (212 F.) and dryer types taught by Dinand et al to dry expanded parenchymal cell wall materials.

The University of Minnesota patent application (Lundberg et al), describes the ability to obtain a functional dried product. However, the only way they were able to obtain a functional dry product was through freeze drying (Gu et al, 2001).—from (Gu, L., R Ruan, P. Chen, W. Wilcke, P. Addis. 2001. *Structure Function Relationships of Highly Refined Cellulose. Transactions of the ASAE*. Vol 44(6): 1707-1712). Freeze drying is not an economically feasible drying operation for large volumes of expanded cell wall products.

The fiber products of the invention may be rehydrated or partially rehydrated so that the highly refined cellulose product is rehydrated to a level of less than 90 g $H_2O$/g fiber mass, 70 g $H_2O$/g fiber mass, 50 g $H_2O$/g fiber mass or rehydrated to a level of less than 30 g $H_2O$/g fiber mass or less than 20 g $H_2O$/g fiber mass. This rehydration process adjusts the functionalities of the product within a target range of at least one property selected from the group consisting of water holding capacity, oil holding capacity, and viscosity and may include the use of a high shear mixer to rapidly disperse organic fiber plant mass materials in a solution. Also the method may include rehydration with soaking of the dry materials in a solution with or without gentle agitation.

The HRC dispersion of the present invention is a highly viscous, semi-translucent gel. HRC embodiments comprise dried powders that are redispersable in water to form gel-like solutions. The functional characteristics of HRC are related to various properties, including water- and oil-retention capacity, average pore size, and surface area. These properties inherently relate to absorption characteristics, but the properties and benefits provided by the processes and products of the invention seem to relate to additional properties created in the practice of the invention.

The present invention also includes an aqueous HRC gel having a lignin concentration of about one to twenty percent (1 to 20%). The HRC products of the present invention exhibit a surprisingly high WRC in the range of about 20 to at least about 56 g $H_2O$/g dry HRC. This high WRC is at least as good as, and in some cases, better than the WRC of prior art products having lower or the same lignin concentrations. The HRC products exhibit some good properties for ORC (oil retention capacity).

A general starting point for a process of preparing the highly refined cellulose materials preferred according to the invention which are then to be treated by enzymatic activity is to start with raw material of sufficiently small size to be processed in the initial apparatus (e.g., where soaking or washing is effected), such as a soaker or vat. The by-product may be provided directly as a result of prior processing (e.g., juice removal, sugar removal, betaine removal, or other processing that results in the fiber by-product. The process of the present invention may also begin when raw material is reduced in size (e.g., chopped, shredded, pulverized) into pieces less than or equal to about 10×5 cm or 5 cm×2 cm. Any conventional type of manual or automated size reduction apparatus (such as chopper, shredder, cutter, slicer, etc.) can be used, such as a knife or a larger commercially-sized chopper. The resulting sized raw material is then washed and drained, thus removing dirt and unwanted foreign materials. The washed and chopped raw material is then soaked. The bath is kept at a temperature of about 20 to 100° C. The temperature is maintained within this range in order to soften the material. In one embodiment, about 100 g of chopped raw material is soaked in a 2.5 liter bath within a temperature range of about 20 to 80 degrees Centigrade for 10 to 90 minutes.

The resulting soaked raw material is subjected to another washing and draining. This washing and additional washing and draining tend to be more meaningful for sugar beets, potatoes, carrots (and to some degree also tomatoes, chicory, apple, pineapple, cranberries, grapes, and the like) than for citrus material. This is because sugar beets, potatoes, carrots, growing on the ground rather than being supported in bushes and trees as are citrus products, tend to pick up more materials from the soil in which they grow. Sugar beets and carrots tend to have more persistent coloring materials (dyes, pigments, minerals, oxalates, etc.) and retained flavor that also are often desired to be removed depending upon their ultimate use. In one embodiment, the soaked raw material is washed with tap water. In one other embodiment, the material is drained. This is optionally followed by bleaching the material with hydrogen peroxide at concentrations of about one (1) to 20% (dry basis) peroxide. The bleaching step is not functionally necessary to effect the citrus and grape fiber conversion to highly refined cellulose. With respect to carrots and sugar beets, some chemical processing may be desirable, although this processing may be significantly less stressful on the fiber than the bleaching used on corn-based HRC products. From our experience, some chemical step is required for sugar beets, and bleaching is one option. Using alkaline pretreatment baths is another option. Acid treatment or another bleaching agent are other options.

The material is optionally bleached at about 20 to 100° C. for about five (5) to 200 min. The bleached material is then subjected to washing with water, followed by filtering with a screen. The screen can be any suitable size. In one embodiment, the screen has a mesh size of about 30 to 200 microns.

The filtered material containing solids can then be refined (e.g., in a plate refiner, stone mill, hammer mill, ball mill, or extruder.). In one embodiment, the filtered material entering the refiner (e.g., a plate refiner) contains about four percent (4%) solids. In another embodiment, the refining can take place in the absence of water being added. The plate refiner effectively shreds the particles to create microfibers. The plate refiner, which is also called a disk mill, comprises a main body with two ridged steel plates for grinding materials. One plate, a refining plate, is rotated while a second plate remains stationary. The plates define grooves that aid in grinding. One plate refiner is manufactured by Sprout Waldron of Muncy, Pa. and is Model 12-ICP. This plate refiner has a 60 horsepower motor that operates at 1775 rpm.

Water may be fed into the refiner to assist in keeping the solids flowing without plugging. Water assists in preventing the refiner's plates from overheating, which causes materials in the refiner to burn. (This is a concern regardless of the type of grinding or shearing device used.). The distance between the plates is adjustable on the refiner. To set refining plate distances, a numbered dial was affixed to the refining plate adjustment handle. The distance between the plates was measured with a micrometer, and the corresponding number on the dial was recorded. Several plate distances were evaluated and the setting number was recorded. A variety of flow consistencies were used in the refiner, which was adjusted by varying solids feed rate. The amount of water flowing through the refiner remained constant. Samples were sent through the refiner multiple times. In one embodiment the materials are passed one or more times through the plate refiner.

The microfibers may then be separated with a centrifuge to produce refined materials. The refined materials are then diluted in water until the solids content is about 0.5 to 37%. This material is then dispersed. In one embodiment, dispersing continues until a substantially uniform suspension is obtained, about 2 to 10 minutes. The uniform suspension reduces the likelihood of plugging.

The resulting dispersed refined materials, i.e., microparticles, may then be homogenized in any known high pressure homogenizer operating at a suitable pressure. In one embodiment, pressures greater than about 5,000 psi are used. The resulting highly refined cellulose (HRC) gel may display a lignin content of about 1 to 20% by weight, depending in part upon its original content.

The absence of use of a mild NaOH soaking before the refining step in the present invention prior to high pressure homogenization does not require the use of high temperature and high pressure cooking (high temperature means a temperature above 100 degrees C. and high pressure means a pressure above 14 psi absolute). High temperature and high pressure cooking may be used, but to the disadvantage of both economics and output of the product. This novel process further avoids the need for either mild concentrations of NaOH or of highly concentrated NaOH and the associated undesirable environmental impact of discharging waste water containing any amount of NaOH and organic compounds. The process also avoids a need for an extensive recovery system. In one embodiment, the pH of the discharge stream in the present invention is only about 8 to 9 and may even approach 7. The method of the present invention has the further advantage of reducing water usage significantly over prior art processes, using only about one third to one-half the amount of water as is used in conventional processes to produce to produce HRC gel and amounts even less than that used in the Chen processes All of the mechanical operations, refining, centrifuging, dispersing, and homogenizing could be viewed as optional, especially in the case of citrus pulp or other tree bearing fruit pulps. Additionally, other shearing operations can be used, such as an extruder, stone mill, ball mill, hammer mill, etc. For citrus pulp, the only processes that are needed to produce the expanded cell structure are to dry (using the novel drying process) and then properly hydrate the raw material prior to the expanding and shearing step of the process of the invention. This simple process could also be used in other raw material sources.

Hydration is a term that means reconstituting the dried fiber back to a hydrated state so that it has functionality similar to the pre-dried material. Hydration can be obtained using various means. For instance, hydration can occur instantly by placing the dry products in a solution followed by shearing the mixture. Examples of shearing devices are a high shear disperser, homogenizer, blender, ball mill, extruder, or stone mill. Another means to hydrate the dry materials is to put the dry product in a solution and mix the materials for a period of time using gentle or minimal agitation. Hydrating dry materials prior to use in a recipe can also be conducted on other insoluble fibrous materials to enhance their functionality.

The initial slurry of fibers/cells from the EPM products is difficult to dry. There is even disclosure in the art (e.g., U.S. Pat. No. 4,413,017 and U.S. Pat. No. 4,232,049) that slurries of such processed products cannot be easily dried without expensive and time consuming processes (such as freeze drying, extended flat bed drying, and the like). Freeze drying is effective, but is not economically and/or commercially desirable. Similarly, tray dryers may be used, but the length of time, labor and energy requirements make the process costly. The slurries of the citrus and/or beet by-products may be dried economically and effectively according to the following practices of the invention. Any type of convective drying method can be used, including a flash dryer, fluid bed dryer, spray dryer, etc. One example of a dryer that can be used is a fluid bed dryer, with dry material being added to the slurry to equilibrate the moisture content in the materials. It has been found that by adding 5:1 to 1:1 dry to wet materials within the fluid bed drier improves the air flow within the drier and the material may be effectively dried. In the absence of the combination of "dry" and "wet" materials, the slurry will tend to merely allow air to bubble through the mass, without effective drying and without a true fluid bed flow in the drier. The terms wet and dry are, of course, somewhat relative, but can be generally regarded as wet having at least (>40% water/<60% solid content] and dry material having less than 20% water/80% solid content). The amounts are not as critical as the impact that the proportional amounts of materials and their respective water contents have in enabling fluid flow within the fluid bed drier. These ranges are estimates. It is always possible to use "wet" material with lower moisture content, but that would have to have been obtained by an earlier drying or other water removal process. For purpose of economy, and not for enabling manufacture of HRC microfibers according to the present invention from citrus or beet by-product, it is more economical to use higher moisture content fiber mass as the wet material. After the mixture of wet and dry materials have been fluid bed dried (which can be done with air at a more moderate temperature than is needed with flat bed dryers (e.g., room temperature air with low RH may be used, as well as might heated air). A flash drier may also be used alternatively or in combination with a fluid bed drier to effect moisture reduction from the citrus or beet by-product prior to produce a functional dry product. It would be necessary, of course, to control the dwell time in the flash drier to effect the appropriate amount of moisture reduction and prevent burning. These steps may be provided by the primary or source manufacturer, or the product may be provided to an intermediate consumer who will perform this drying step to the specification of the process that is intended at that stage.

One aspect of the drying process is useful for the drying of any expanded cellulose products, especially for the drying of highly refined cellulose fibers and particles that have been extremely difficult or expensive to dry. Those products have been successfully dried primarily only with freeze drying as a commercially viable process. That process is expensive and energy intense. A method according to the present invention for the drying of any expanded cellulose fiber or particle product comprises drying an expanded cellulose product by providing a first mass of expanded cellulose fiber product having a first moisture content as a weight of water per weight of fiber solids; providing a second mass of expanded cellulose fiber product having a second moisture content as a weight of water per weight of fiber solids, the second moisture content being at least 20% less than said first moisture content; combining said first mass of expanded cellulose fiber product and said second mass of expanded cellulose product to form a combined mass; drying said combined mass in a drying environment to form a dried combined mass. The method may have the dried combined mass dried to a moisture content of less than 20, less than 10, less than 8, less than 5 or less than 3 $H_2O$/g fiber mass. The method, by way of non-limiting examples, may use drying environments selected from the group consisting of, flash driers, fluid bed driers and combinations thereof.

The rehydration and shearing (particularly high shearing at levels of at least 10,000 $sec^{-1}$, preferably at least 15,000 $sec^{-1}$, more often, greater than 20,000, greater than 30,000, greater than 40,000, and conveniently more than 50,000 $sec^{-1}$ (which is the actual shearing rate used in some of the examples) of the dry fiber product enables the resultant sheared fiber to retain more moisture and to retain moisture more strongly. It has been noted in the use of materials according to the practice of the invention that when the fiber products of the invention are rehydrated, the water activity level of rehydrated fiber is reduced in the fiber (and the fiber present in a further composition) as compared to free water that would be added to the further composition, such as a food product. The food products that result from cooking with 0.1 to 50% by weight of the HRC fiber product of the invention present has been found to be highly acceptable to sensory (crust character, flavor/aroma, grain/texture, taste, odor, and freshness, especially for mixes, frozen foods, baked products, meat products and most particularly for bakery goods, bakery products, and meat products) tests on the products. Importantly, the products maintain their taste and mouth feel qualities longer because of the higher moisture retention.

An amount of plant mass, fiber material or highly refined cellulose that is "effective to enhance viscosity" means an amount of highly refined cellulose or enzymatically modified refined or highly-refined cellulose particles that provides increased viscosity in an aqueous liquid, as measured by, for example, by any conventional viscosity measuring technique. A standard basis for measuring viscosity in the evaluations and comparisons in the present technology is as follows.

Viscosity Measuring Procedure

Measure the viscosity using a Brookfield DV II+ viscometer using cylindrical spindles at 10 rpm with a 3% by weight solids/water solution at room temperature (25° C.±3° C.) for 1 minute (measurements may be done over as long a time period as desirable, but the 1 minute minimum should assure distribution of the fibers through the aqueous system. Stirring and measuring for a time period extending over 2 minutes, 5 minutes, 10 minutes, 15 minutes, 30 minutes or an hour are useful measurements and standards.

Any suitable amount of plant mass, fiber material (in particle or fiber or fibrid form) or highly refined cellulose effective to increase viscosity in the aqueous liquid may be used. In a preferred embodiment, the highly refined cellulose component is present in the aqueous liquid an amount sufficient to provide greater than or equal to about 0.005% w/w highly refined cellulose, more preferably from greater than about 0.1% w/w, and still more preferably from about 0.2% w/w to about 1% w/w highly refined cellulose concentration in the product. Unless otherwise specified, the concentrations of highly refined cellulose given herein are based on the weight of non-hydrated highly refined cellulose. No matter which process is used, any amount of highly refined cellulose effective to provide a measurable increase in viscosity (based on about 100% w/w of the liquid composition to which the enzymatically modified refined cellulose is added) from about 1% w/w to about 30% w/w composition, from about 30% w/w to about 80% w/w water, up to about 50% w/w composition, and from about 0.005% w/w to about 3.0% w/w highly refined cellulose, should be used.

Suitable aqueous plant mass, fiber or highly refined cellulose compositions are made by blending the components of the solution in water. In one embodiment, the plant mass, fiber or aqueous highly refined cellulose composition consists essentially of highly refined cellulose in water. As used herein, the term "water" generally refers to tap water, that is, water as available onsite without requiring purification that may contain minor amounts of components other than H2O. However, any suitable water may be used.

In a preferred embodiment, the aqueous treatment solution is such that it provides greater than or equal to about 0.005% w/w highly refined cellulose concentration, more preferably about greater than about 0.1% w/w, and most preferably from about 0.2% w/w to about 1% w/w highly refined cellulose concentration in the aqueous composition product. Accordingly, a preferred aqueous treatment solution comprises greater than or equal to about 0.05 percent by weight (wt %) of the highly refined cellulose composition more preferably from about 0.1 wt %, still more preferably from about 0.2 wt % to about 15 wt %, and even more preferably from about 0.47 wt % to about 6 wt %, highly refined cellulose, wherein the ranges are calculated on the basis of the weight of the enzymatically modified anhydrous highly refined cellulose.

The aqueous highly refined cellulose composition may, optionally, further comprise other components, such as for example, alkali metal silicates, alkali metal salts, such as for example, NaCl, KCl, and surfactants suitable for food use and other viscosity modifiers.

In a preferred embodiment, the aqueous composition exhibits a pH of from about 10 to about 14, more preferably from about 11 to about 13.5, even more preferably from about 11.4 to about 13.

Also, in a preferred embodiment, the aqueous highly refined cellulose composition is at a temperature of from about 0° C. to about 85° C., more preferably from 0° C. to about 70° C., still more preferably from about 0° C. to about 50° C., and even more preferably from about 0° C. to about 20° C.

It should also be appreciated that the compositions of the solutions and methods used in the process of the invention may be varied according to the desired characteristics of the food product. The following non-limiting examples will further illustrate the preparation and performance of the invention. However, it is to be understood that these examples are given by way of illustration only and are not a limitation of the invention.

EXAMPLES

Preparation Examples of Highly Refined Cellulose Materials by Preferred Processes

Example 1

Dried beet pulp shreds were obtained from a local feed store. The beet pulp was then ground to a powder using a disk mill or refiner. One particularly useful plate refiner is manufactured by Sprout Waldron of Muncy, Pa. and is Model 12-ICP. This plate refiner has a 60 horsepower motor that operates at 1775 rpm. After the dry materials were ground, they were soaked in hot water at 100° C. for 5 minutes at 5% solids, where the materials started to absorb moisture. The soaked materials were then washed with water in a screen cart to remove any unwanted particulate or soluble materials. After soaking, the materials were diluted to 3% solids and bleached in a 150 gallon (555 liter) tank with agitation. The bleaching conditions were 15% hydrogen peroxide (based on dry matter weight), a pH of 11.5, and a temperature of 80° C. for one hour. After bleaching, the material was then washed in a screen cart. After bleaching, the materials were then refined again at 3% solids using the same refiner in the first step, which was followed by further reducing particle sizes in an IKA Dispax Reactor, Model DR 3-6A (Wilmington, N.C.). The dispersed materials were then homogenized three times at 8000 psi (approximately $5 \times 10^5$ $sec^{-1}$ shear rate) using a APV Gaulin high pressure homogenizer, Model MC(P)-45 (Wilmington, Mass.). The homogenized materials were then dried at 120° F. in a Harvest Saver Dehydrator made by Commercial Dehydrator Systems (Eugene, Oreg.). The dried materials were then ground in a Fitzmill, Model D6 (Elmhurst, Ill.), with a 0.050 inch (0.12 cm) round 22 gauge 316 mesh stainless steel screen. After grinding, the ground materials were then rehydrated at 1% solids using a standard kitchen household blender on high speed for three minutes. Viscosity was then measured using a Brookfield LVDV++ viscometer (Middleboro, Mass.) with cylindrical spindles. Keltrol xanthan and propylene glycol alginate (PGA) were obtained from CP Kelco. 1% solutions were made by mixing the materials in a blender for 3 minutes. Rheology was determined using the same Brookfield viscometer. The results are shown in FIG. 1. This data shows that the fibers of the invention are capable of providing a viscosity of at least 23,000 at a concentration of 1% fibers derived from sugar beets at 1 rpm at 20° C. It is within the skill of the artisan using the teachings of this invention to provide viscosities of greater than 24,000 and greater than 25,000 at these concentrations and conditions to produce the parenchymal cell based highly refined cellulose fibers of the invention. This is evidence by FIG. 1.

FIG. 1 describes a Comparison of rheology curves for Fiberstar's processed beet pulp versus xanthan and PGA (propylene glycol alginate).

Citrus Examples 2-6

Example 2

Frozen washed orange pulp cells were obtained from Vita Pakt (Covina, Calif.). Hot water was added to the frozen pulp to thaw the pulp. After thawing, the materials were dewatered on a screen to remove any excess water and bring the solids content to 5%. The thawed and screened materials were refined using a Sprout Waldron disk mill (Muncy, Pa.), Model 12-ICP. The refined materials were then dispersed at 5% solids at 50,000 $sec^{-1}$ shear rate using an IKA Dispax™ Reactor, Model DR 3-6A (Wilmington, N.C.). Viscosity was then measured using a Brookfield LVDV++ viscometer (Middleboro, Mass.) with cylindrical spindles.

Example 3

Frozen washed orange pulp cells were obtained from Vita Pakt™ (Covina, Calif.). Hot water was added to the frozen pulp to thaw the pulp. After thawing, the materials were dewatered on a screen to remove any excess water and produce a pulp with a 5% solids content. The thawed and screened materials were refined at 5% solids using a Sprout Waldron disk mill (Muncy, Pa.), Model 12-ICP. The refined materials were then dispersed using an IKA Dispax™ Reactor, Model DR 3-6A (Wilmington, N.C.) at 5% solids. The dispersed materials were then homogenized one time at 8000 psi using an APV Gaulin high pressure homogenizer, Model MC(P)-45 (Wilmington, Mass.) at 5% solids. Viscosity was then measured using a Brookfield LVDV++ viscometer (Middleboro, Mass.) with cylindrical spindles.

Example 4

Frozen washed orange pulp cells were obtained from Vita Pakt™ (Covina, Calif.). Hot water was added to the frozen pulp to thaw the pulp. After thawing, the materials were dewatered on a screen to remove any excess water and produce a pulp with a 5% solids content. The thawed and screened materials were refined at 5% solids using a Sprout Waldron disk mill (Muncy, Pa.), Model 12-ICP. The refined materials were then dispersed using an IKA Dispax™ Reactor, Model DR 3-6A (Wilmington, N.C.) at 5% solids. The dispersed materials were then homogenized one time at 8000 psi (approximately $5 \times 10^5$ $sec^{-1}$ shear rate) using an APV Gaulin high pressure homogenizer, Model MC(P)-45 (Wilmington, Mass.) at 5% solids. The homogenized materials were then dried at 70° F. (21° C.) in a Harvest Saver™ Dehydrator made by Commercial Dehydrator Systems (Eugene, Oreg.). The dried materials were then ground in a Fitzmill, Model D6 (Elmhurst, Ill.), with a 0.050 inch round 22 gauge 316 stainless steel screen. After grinding, the ground materials were then rehydrated at 1% solids using a standard kitchen household blender on high speed for three minutes. Viscosity was then measured using a Brookfield LVDV++ viscometer (Middleboro, Mass.) with cylindrical spindles.

Example 5

Frozen washed orange pulp cells were obtained from Vita Pakt™ (Covina, Calif.). Hot water was added to the frozen pulp to thaw the pulp. After thawing, the materials were dewatered on a screen to remove any excess water and produce a pulp with a 5% solids content. These materials were then put in a blender on high speed for 3 minutes (approximately 30,000 to 40,000 $sec^{-1}$ shear rate) and the viscosity was then measured using a Brookfield LVDV++ viscometer (Middleboro, Mass.) with cylindrical spindles.

Example 6

Frozen washed orange pulp cells were obtained from Vita Pakt™ (Covina, Calif.). Hot water was added to the frozen pulp to thaw the pulp. After thawing, the materials were dewatered on a screen to remove any excess water and produce a pulp with a 5% solids content. The thawed materials were then dried at 70° F. (21° C.) in a Harvest Saver Dehydrator made by Commercial Dehydrator™ Systems (Eugene, Oreg.). The dried materials were then ground in a Fitzmill, Model D6 (Elmhurst, Ill.), with a 0.050 inch (0.12 cm) round 22 gauge 316 mesh stainless steel screen. After grinding, the ground materials were then rehydrated at 1% solids using a standard kitchen household blender on high speed for three minutes (approximately 30,000 to 40,000 sec$^{-1}$ shear rate). Viscosity was then measured using a Brookfield LVDV++ viscometer (Middleboro, Mass.) with cylindrical spindles.

Table Showing Viscosities of Citrus Pulp Cells after Various Treatment Conditions.

|  |  | Viscosity (cP) | |
| --- | --- | --- | --- |
| Example # | Solids % | 0.5 rpm | 10 rpm |
| 2) | 1% | 15207 | 1428 |
| 3) | 1% | 15477 | 1966.5 |
| 4) | 1% | 8728 | 587.5 |
| 5) | 1% | 15117 | 1608 |
| 6) | 1% | 10275 | 999 |

Example 7

Dry Product Rehydration Using Production Size Equipment

Quadro™ (Milburn, N.J.) [rehydrated dry orange pulp product at 3% solids and ran the mixture through their Model Z3 emulsifier various times. As shown in the following table, one pass through their emulsifier is more effective than rehydrating by shearing 3.5 minutes in a blender. With this style machine, our product is fed into the disperser feeder, where it drops into the water stream, gets hydrated, and goes directly to the ingredient mix without the need for an allocated dispersing tank and can be sized to rehydrate on a large production scale.

Table Showing Viscosity (3% Solids) for Various Passes Through a High Shear Emulsifier] Vs a Kitchen Blender.

| Shearing Method | Viscosity (cP), 3% | | | | |
| --- | --- | --- | --- | --- | --- |
|  | 0.5 rpm | 10 rpm | 60 rpm | 100 rpm | 200 rpm |
| Disp, 1 pass | 25,375 | 1,923 | 405 | 260.1 | 138.5 |
| Disp, 2 passes | 36,172 | 1,668 | 473 | 335 | 191 |
| Disp, 3 passes | 35,512 | 1776 | 525 | 340 | 185.1 |
| Blender, 3.5 min | 17,396 | 1617 | 321.9 | 218.4 | 138 |

Example 8

Dried citrus peel and/or beet fiber products commonly sold today for a fiber source can also be processed and produce a functional product. A dry ground citrus peel product was obtained from Vita Pakt™ (Covina, Calif.). The dry ground citrus peel was then dispersed at 3% solids using an IKA Dispax™ Reactor, Model DR 3-6A (Wilmington, N.C.) at 5% solids. The dispersed materials were then homogenized one time at 8000 psi using an APV Gaulin high pressure homogenizer, Model MC(P)-45 (Wilmington, Mass.). Viscosity was then measured using a Brookfield LVDV++ viscometer (Middleboro, Mass.) with cylindrical spindles.

| | Viscosity (cP), 3% | | | | |
| --- | --- | --- | --- | --- | --- |
| Method | 0.5 rpm | 10 rpm | 60 rpm | 100 rpm | 200 rpm |
| Dry product in water | <10 | <10 cP | <10 cP | <10 cP | <10 Cp |
| Dry product after shearing | 1666 | 213 | 65 | 44 | 29 |

Example 9

Fluid Bed Drying

Fluid bed drying trials were performed using a Carrier Vibrating Equipment (Louisville, Ky.) a one square (foot vibrating fluid bed dryer. Dry products were attained having functionality that was near identical to the wet feed materials. The drying tests were conducted using 100-140° F. (38-60° C.) outlet air temperatures, 400° F. (205° C.) air inlet temperatures, and residence times in the dryer were around 5-25 minutes. All materials that underwent drying were dried to less than 15% moisture. All viscosities were measured at 1% using a Brookfield LVDV++ viscometer (Middleboro, Mass.) with cylindrical spindles. Prior to drying, the wet materials need to be back mixed (that is wetter materials are added to the drier materials to facilitate drying of the wetter materials) with the dry materials (backmix ratio was 2 parts dry to 1 part wet) and a total of 6 lbs (2.6 kg) of wet feed was put in the batch style dryer. The results from the testing are shown below:

| Drying Conditions | Moisture % | Viscosity (cP), 1% | | | | |
| --- | --- | --- | --- | --- | --- | --- |
|  |  | 0.5 rpm | 10 rpm | 60 rpm | 100 rpm | 200 rpm |
| Feed material | 39.5 | 5020 | 577 | 220 | 155 | 87 |
| 400 F. drying air | 12.2 | 5929 | 515 | 178 | 145 | 80 |

Example 10

Flash Drying

Pilot scale Flash drying trials were performed using a Carrier Vibrating Equipment (Louisville, Ky.) Tornesh dryer. Prior to drying, the wet materials (dispersed orange pulp, as from Example 2) were to be back mixed with the dry materials, again orange pulp from Example 2 (backmix ratio was 2 parts dry to 1 part wet) and a total of 30 lbs (13 kg) of 50% moisture wet feed was put in the dryer. Dry products were attained having functionality that was similar to the wet feed materials. The drying tests were conducted using 200° F. (94° C.) outlet air temperatures and residence times in the dryer were around 1-3 minutes. The dried materials were rehydrated using a blender on high speed for 3 minutes and all viscosities were measured at 1% using a Brookfield LVDV++ viscometer (Middleboro, Mass.) with cylindrical spindles. The results from the testing are shown below:

| Drying Conditions | Moisture % | Viscosity (cP), 1% | | | | |
|---|---|---|---|---|---|---|
| | | 0.5 rpm | 10 rpm | 60 rpm | 100 rpm | 200 rpm |
| Feed material | 39.5 | 5020 | 577 | 220 | 155 | 87 |
| Flash dried feed materials (400 F. air) | 13.9 | 4232 | 368 | 134 | 88 | 53 |

Product Use Examples of Enzymatically Modified Fibers and Highly Refined Cellulose Pectinase or pectinases are any enzyme that breaks down pectin, a polysaccharide substrate found in the cell wall of plants, into simple sugars and galacturonic acid. It is commonly used in fruit industry that involves degradation of plant materials to speed up extraction of juices from fruits. Pectinases are also used for retting. Addition of chelating agents or pretreatment of the plant material with acid enhances the effect of the enzyme.

There are many classes of enzymes, such as the active enzymes of a lyase, a ligase, a hydrolase, an oxidoreductase, a transferase, or an isomerase, and more preferably the enzyme is an amylolytic enzyme, a lipolytic enzyme, a proteolytic enzyme, a cellulytic enzyme, an oxidoreductase or a plant cell-wall degrading enzyme, and more preferably an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

There are several different enzymes that have the ability to modify pectin; these are the pectinases, pectin methylesterases, pectin lyases and pectate lyases. The term "pectate lyase" includes all polypeptides having a pectate lyase, or pectinase, activity, including the beta-elimination (trans-elimination) and/or hydrolysis of pectin and/or polygalacturonic acid (pectate) or other plant wall constituents, e.g., homogalacturonan or rhamnogalacturonan, including 1,4-linked alpha-D-galacturonic acid. In one aspect, pectate lyase activity includes catalysis of the cleavage of glycosidic linkages of pectic substances, e.g., catalyzing the beta-elimination (trans-elimination) and/or hydrolysis of plant cell walls (e.g., the breakup or dissolution of cell walls comprising pectin, e.g., plant cell walls). In one aspect, pectate lyase activity includes catalyzing the beta-elimination (trans-elimination) and/or hydrolysis of methyl-esterified galacturonic acid, including partially or completely methyl-esterified polygalacturonic acid. In one aspect, the pectate lyase activity is mainly endo-acting, e.g., cutting the polymer (e.g., polygalacturonic acid) at random sites within a chain to give a mixture of oligomers, or the pectate lyase activity may be exo-acting, attacking from one end of the polymer and producing monomers or dimers, or, a combination thereof. In one aspect, the pectate lyase activity comprises catalyzing the random cleavage of alpha-1,4-glycosidic linkages in pectic acid (polygalacturonic acid) by trans-elimination. In one aspect, pectate lyase activity includes polypeptides having activity the same or similar to pectate lyase (EC 4.2.2.2), poly(1,4-alpha-D-galacturonide) lyase, polygalacturonate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and/or exo-poly-alpha-galacturonosidase (EC 3.2.1.82).

A polypeptide can be routinely assayed for pectate lyase activity (e.g., tested to see if the protein is within the scope of the invention) by any method, e.g., a PGA assay for pectate lyases. In this test pectate lyase activity is measured at desired temperature and pH using 0.2% polygalacturonic acid (Sigma, P3850) in 25 mM TrisHCl-mM Glycine NaOH buffer. One unit of enzyme activity is defined as the amount of protein that produced 1.mu.mol of unsaturated oligogalacturonides per minute equivalent to 1.mu.mol of unsaturated digalacturonide, using molecular extinction coefficient value of 4600 $M^{-1}$ $cm^{-1}$ at 235 nm for dimer. Protein can be determined for homogenous purified protein by measuring absorbance at 280 nm, using extinction coefficient value specific for each protein based on sequence. US Published Patent Application document 201000021988 (Kerovuo) discloses the use of pectinases to increase the yield of Fruit juices.

Example 11

Specific amounts of wet pulp were blended for 3 minutes with water to create 3% solid content pulp mixture. All samples were approximately 250 ml and placed inside glass jars. The jars were placed in a water bath at appropriate temperatures (e.g., 20° C. to 75° C., or 15° C. to 80° C., or 25° C.-75° C.) although broader ranges may be used, affecting the speed and quality of the reaction) for one hour. The samples were allowed to return to room temperature and viscosities were taken. Graduated cylinders and plastic pipettes were used to measure the volume of enzyme.

The first test ran contained 7 samples, a control and 6 samples with Pectinex™ Ultra SP-L. They were placed in a water bath of 45±3° C. for one hour. The second test consisted of 7 samples ranging from 0-20 drops of enzyme and was place in the same hot water bath for one hour. It was assumed that 20 drops is equivalent to 1 ml.

The pH tests were conducted in the same conditions with 2 ml of enzyme added. The pH was altered to the desired level using Citric Acid and Sodium Hydroxide. The first test was conducted between pH levels of 3 and 9 at increments of 1. The second test narrowed in on the peak and was conducted between pH levels of 4 and 7 with increments of 0.5.

Temperature tests were conducted with 2 samples each containing 2 ml of enzyme. They were placed in a water bath at temperatures from 20-70° C. for one hour.

The time trials were conducted at 40±3° C. For each time length two samples were tested containing 2 ml of enzyme. The times were in 30 minute increments from 30-120 minutes.

Results and Discussion

Concentration Tests: FIG. 1

| Ml | initial | after | % change | 96 hrs later | % change sitting | total % change |
|---|---|---|---|---|---|---|
| 0 | 4511 | 5303 | 17.56% | 3263 | −38.47% | −27.67% |
| 1 | 4523 | 3441 | −23.92% | 1179 | −65.74% | −73.93% |
| 1.75 | 5099 | 3311 | −35.07% | 812.8 | −75.45% | −84.06% |
| 2.5 | 3887 | 1891 | −51.35% | 223.8 | −88.16% | −94.24% |
| 5 | 3567 | 1426 | −60.02% | 144.8 | −89.85% | −95.94% |
| 7.5 | 3651 | 851.9 | −76.67% | 30 | −96.48% | −99.18% |
| 10 | 3241 | 563.9 | −82.60% | 60 | −89.36% | −98.15% |

-continued

| Ml | initial | after | % change | 96 hrs later | % change sitting | total % change |
|---|---|---|---|---|---|---|

Figure 2:
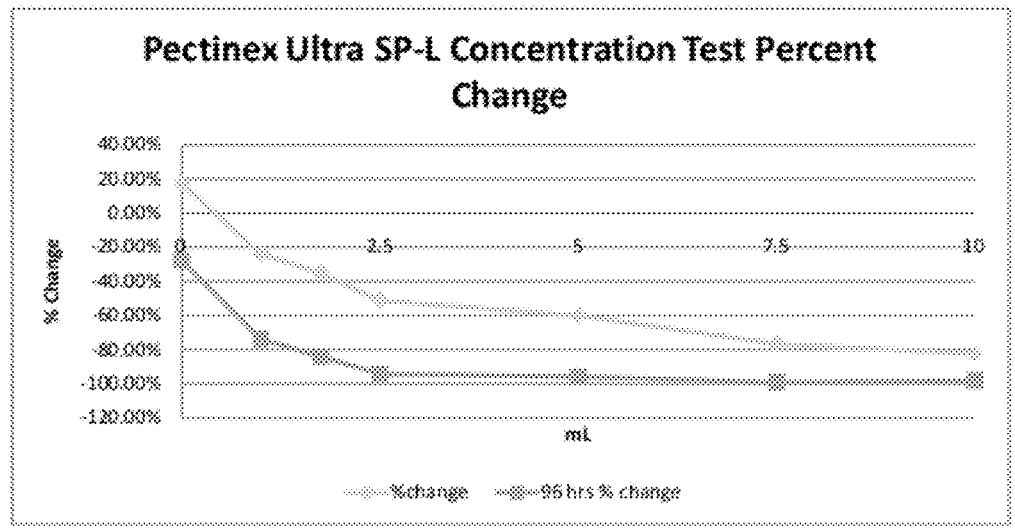
FIG. 2 shows graphing of properties of treated materials according to the present technology.

At lower enzyme levels Pectinex Ultra SP-L requires more time to fully react and can benefit from long sitting times. At higher concentration levels the pulp can become grainy. Levels above 6.667% are in excess. FIG. 2

Figure 3:
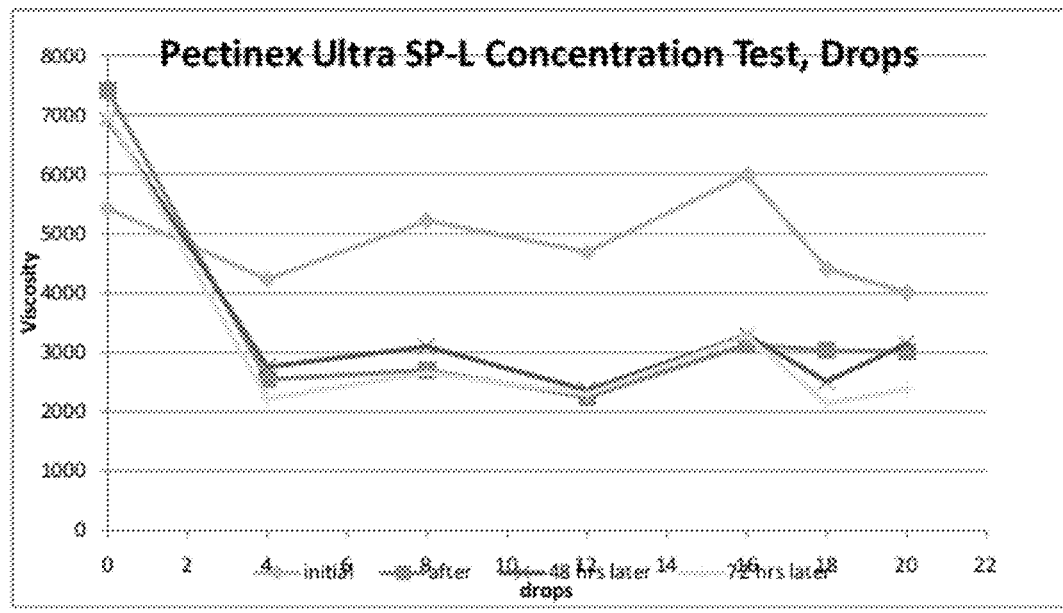
FIG. 3 shows graphing of properties of treated materials according to the present technology.

| drops | initial | after | % change | 48 hrs later | 48 hrs % change | 72 hrs later | 72 hrs % change |
|---|---|---|---|---|---|---|---|
| 0 | 5423 | 7414 | 36.71% | 6935 | 27.88% | 7008 | 29.25% |
| 4 | 4229 | 2545 | −39.82% | 2754 | −34.88% | 2218 | −47.55% |
| 8 | 5219 | 2699 | −48.29% | 3094 | −40.72% | 2651 | −49.20% |
| 12 | 4691 | 2244 | −52.16% | 2360 | −49.69% | 2290 | −51.18% |
| 16 | 5989 | 3131 | −47.72% | 3287 | −45.12% | 3271 | −45.38% |
| 18 | 4407 | 3032 | −31.20% | 2507 | −43.11% | 2136 | −51.53% |
| 20 | 4007 | 3007 | −24.96% | 3147 | −21.46% | 2380 | −40.60% | pH Testing: FIG. 3

| pH | initial | After | % change | 48 hrs | % change |
|---|---|---|---|---|---|
| 3.02 | 6791 | 2931 | −56.84% | 2184 | −67.84% |
| 4.06 | 8254 | 4653 | −55.74% | 2927 | −64.54% |
| 4.91 | 7730 | 2975 | −61.51% | 1394 | −83.26% |
| 5.98 | 5291 | 2932 | −44.59% | 959.7 | −81.86% |
| 6.97 | 6479 | 2855 | −55.93% | 1159 | −82.11% |
| 8.00 | 5079 | 2232 | −56.05% | 902.8 | −82.22% |
| 9.13 | 4857 | 2040 | −58.00% | 749.8 | −84.56% |
| 3.98 | 4307 | 2118 | −50.82% | 1836 | −57.37% |
| 4.5 | 4767 | 2052 | −56.95% | 1728 | −63.75% |
| 5.06 | 5131 | 2615 | −49.04% | 1596 | −68.89% |
| 5.51 | 5179 | 2939 | −43.25% | 2251 | −56.54% |
| 6.01 | 5981 | 3329 | −44.34% | 3047 | −49.06% |
| 6.51 | 4703 | 2501 | −46.82% | 2196 | −53.31% |
| 7 | 5149 | 2803 | −45.56% | 3047 | −40.82% |

Optimum pH is 4.5-5. Outside a range of 4-6 the enzyme can become denatured.

Figure 4:
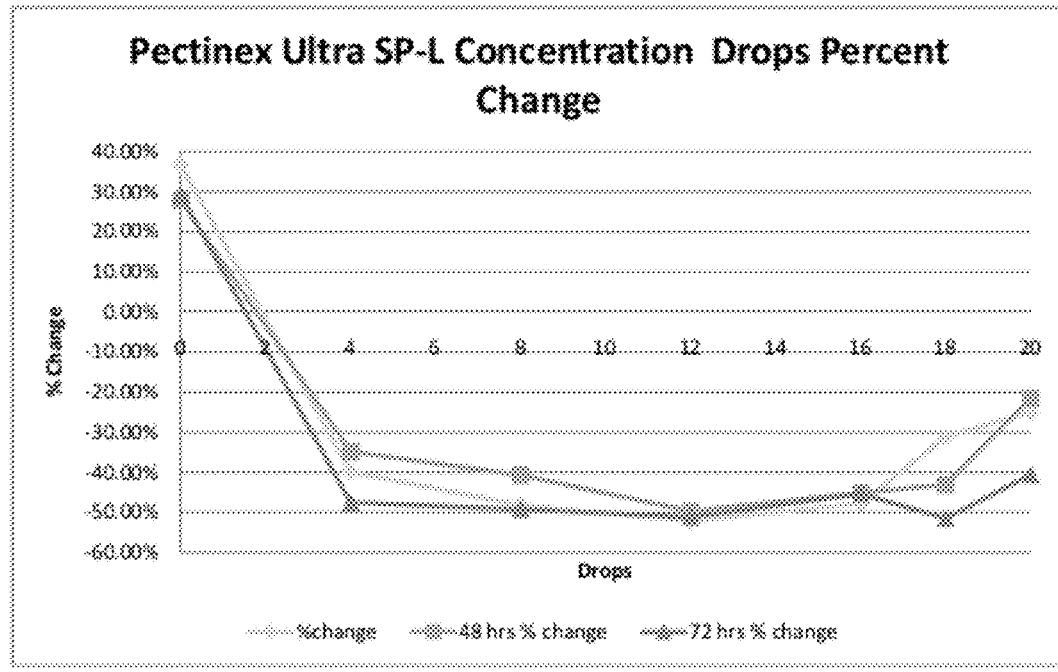
FIG. 4 shows graphing of properties of treated materials according to the present technology.
Figure 7:
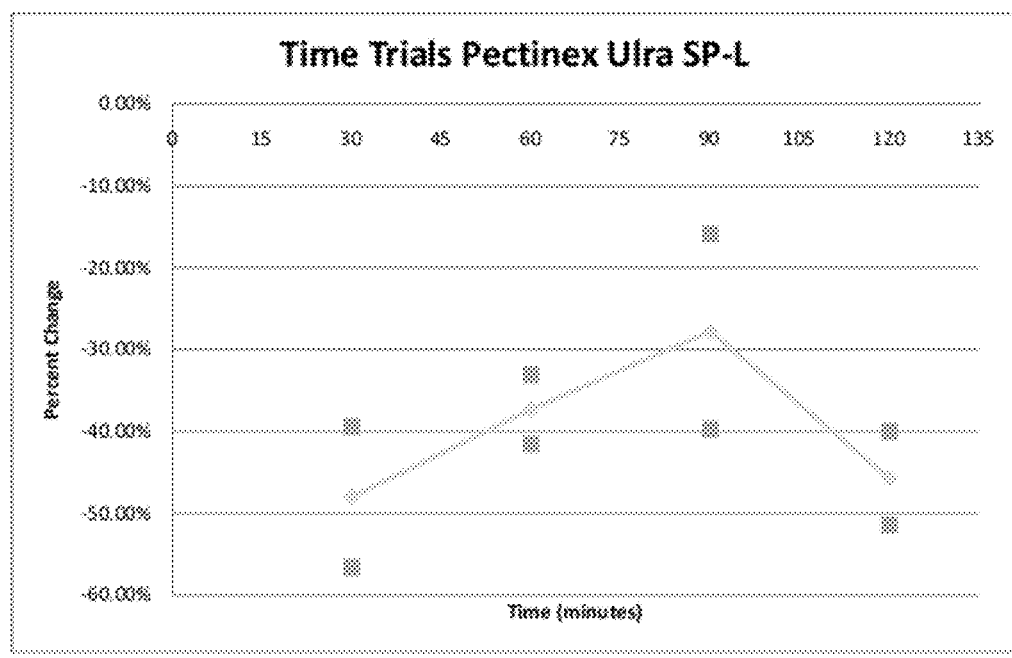
FIG. 7 shows graphing of properties of treated materials according to the present technology.

Temperature Testing: FIG. 4

| temp | Initial | After | % change |
|---|---|---|---|
| 20 | 6441 | 5135 | −20.28% |
| 20 | 5567 | 2597 | −53.35% |
| 30 | 5803 | 2891 | −50.18% |
| 30 | 5723 | 2637 | −53.92% |
| 40 | 5799 | 1452 | −74.96% |
| 40 | 6455 | 2579 | −60.05% |
| 50 | 7254 | 3899 | −46.25% |
| 50 | 6728 | 3611 | −46.33% |
| 60 | 6491 | 5561 | −14.33% |
| 60 | 6149 | 4592 | −25.32% |
| 70 | 5387 | 3911 | −27.40% |

| temp | % change |
|---|---|
| 20 | −36.81% |
| 30 | −52.05% |
| 40 | −67.50% |
| 50 | −46.33% |
| 60 | −19.82% |
| 70 | −27.40% |

Time Trails: FIG. 5

| minute | Initial | After | % change |
|---|---|---|---|
| 30 | 1824 | 791.5 | −56.61% |
| 30 | 1704 | 1032 | −39.44% |
| 60 | 1560 | 911.8 | −41.55% |
| 60 | 1524 | 1020 | −33.07% |
| 90 | 1440 | 1212 | −15.83% |
| 90 | 1512 | 911.8 | −39.70% |
| 120 | 1704 | 827.8 | −51.42% |
| 120 | 1680 | 1008 | −40.00% |

| min | average |
|---|---|
| 30 | −48.02% |
| 60 | −37.31% |
| 90 | −27.76% |
| 120 | −45.71% |

One advantage of the present technology is that ordinarily when manufacturing bulk amounts of final product, viscosity must be controlled by determining the specific effects of specific amounts of the different viscosity modifying agents per volume. By modifying the viscosity enhancing properties of an additive, as done with the present technology, different subclasses of essentially the same chemical composition of additive may be produced whereby a consistent volume of the present novel additive can be added, while the degree of change in viscosity can be accurately predicted by the specific properties or degree of enzymatic-modification effected on the highly refined cellulose starting material. In this way, a final product with a sp4ecifically desired viscosity can be produced without altering the underlying product composition percentages by adding one of the subclasses of viscosity enhancing compositions of the present technology in a constant volume.

The viscosity modifying compositions of the present technology may be used as a dry additive to other aqueous products or may be rehydrated or partially rehydrated as a liquid additive to be provided to other products that may be aqueous or not. Among the classes of products with which this composition may be used include, but are not limited to, dairy products—sour cream, cream cheese, cheese, ice cream, yogurt, butter, ice cream; beverages; soups; stews; frostings, créme fillings, icings; sauces; mayonnaise; fruit purees, jams, jellies; reduced fat or thickened margarines, shortenings, and spreads; a personal care and industrial (e.g. paint, varnish, coatings, sprays, ointments, skin care products, shampoos) and other products as well.

Enzyme Increasing Example

Specific amounts of wet pulp were blended for 3 minutes with water to create 3% solid content pulp mixture. All samples were approximately 250 ml and placed inside glass jars. The jars were placed in a water bath at appropriate temperatures for one hour. The samples were allowed to return to room temperature and viscosities were taken. Graduated cylinders and plastic pipettes were used to measure the volume of enzyme. "Enzymatic-modification" means treating the fiber with an enzyme that chemically alters the plant mass or material within the plant mass and resulting in a change in viscosity, The first test ran contained 4 samples, a control and 3 samples with NovoShape. The three samples contained, 2.5 ml-10 ml of the enzyme. They were placed in a water bath of 45±3° C. for one hour. The second test consisted of 7 samples ranging from 0-20 drops of enzyme and was place in the same hot water bath for one hour. It was assumed that 20 drops is equivalent to 1 ml.

The pH tests were conducted in the same conditions with 0.5 ml of enzyme added. The pH was altered to the desired level using Citric Acid and Sodium Hydroxide. The first test was conducted between pH levels of 3 and 9 at increments of 1. The second test narrowed in on the peak and was conducted between pH levels of 3.5 and 6 with increments of 0.5.

Temperature tests were conducted with 2 samples each containing 0.5 ml of enzyme. They were placed in a water bath at different temperatures for one hour.

The time trials were conducted at 40±3° C. For each time length two samples were tested containing 2 ml of enzyme. The times were in 30 minute increments from 30-120 minutes.

Results and Discussion

Concentration Test:

| Ml | initial | after | % change | 24 hrs | % change from sitting | total % change |
|---|---|---|---|---|---|---|
| 0 | 3407 | 4307 | 26.42% | 4341 | 0.79% | 27.41% |
| 2.5 | 6507 | 35273 | 442.08% | 38913 | 10.32% | 498.02% |
| 5 | 4907 | 50569 | 930.55% | 88711 | 75.43% | 1707.85% |
| 10 | 6635 | 110000 | 1557.87% | 114000* | 3.64% | 1618.16% |

Extremely high viscosities are possible given enough enzymes. With high enzyme concentrations the pulp turns into a gel that retains the shape of the jar. NovoShape reacts very quickly. Within a few minutes the viscosity can change dramatically. The viscosity increase so much that the viscometer was not able to get a reading on the sample with 10 ml. The viscosity is even higher for than the table shows.

| Viscosity Concentration Test | | | | | |
|---|---|---|---|---|---|
| drops | initial | after | 1 hr | 2 hrs | 3 hrs |
| 0 | 3347 | 2975 | 3347 | 2987 | 2783 |
| 4 | 2675 | 3501 | 4119 | 4451 | 4344 |
| 8 | 3515 | 4679 | 5339 | 5291 | 5327 |
| 12 | 3119 | 5029 | 5907 | 5873 | 5637 |
| 16 | 3851 | 6578 | 6969 | 7386 | 8002 |
| 18 | 3268 | 5737 | 6517 | 9334 | 11128 |
| 20 | 3719 | 6631 | 9012 | 11478 | 11875 |

Figure 8:
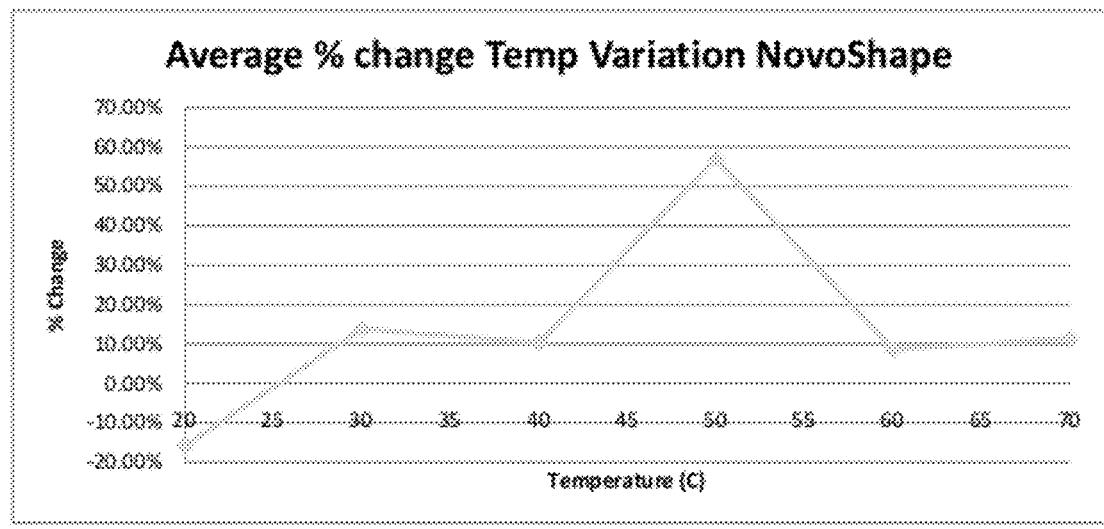
FIG. 8 shows graphing of properties of treated materials according to the present technology.

The viscosity was measured every hour for 3 hours after the samples were heated to see how quickly viscosity increased and if resting time was beneficial or not. It appears that for lower concentrations the enzyme does not need to additional time to reach the full effect. This is confirmed by the percent change data. FIG. 8

| % Change Drop Wise Test | | | | |
|---|---|---|---|---|
| drops | % change cooking | % change 1 hr | % change 2 hr | % change 3 hr |
| 0 | -11.11% | 0.00% | -10.76% | -16.85% |
| 4 | 30.88% | 53.98% | 66.39% | 62.39% |
| 8 | 33.12% | 51.89% | 50.53% | 51.55% |
| 12 | 61.24% | 89.39% | 88.30% | 80.73% |
| 16 | 70.81% | 80.97% | 91.79% | 107.79% |
| 18 | 75.55% | 99.42% | 185.62% | 240.51% |
| 20 | 78.30% | 142.32% | 208.63% | 219.31% | pH Testing:

| pH Test | initial | after | % change |
|---|---|---|---|
| 3.01 | 7181 | 6995 | -2.59% |
| 4.05 | 6539 | 7329 | 12.08% |
| 5.09 | 6631 | 7930 | 19.59% |
| 5.97 | 5891 | 6491 | 10.19% |
| 6.93 | 7570 | 7334 | -3.12% |
| 8.11 | 6801 | 6709 | -1.37% |
| 9.04 | 7703 | 7222 | -6.24% |
| 3.42 | 6263 | 7066 | 12.82% |
| 3.92 | 5831 | 6692 | 14.77% |
| 4.53 | 6632 | 9970 | 50.33% |
| 4.96 | 6713 | 8011 | 19.34% |
| 5.56 | 8529 | 8490 | -0.46% |
| 6.07 | 7958 | 7389 | -7.15% |

Figure 9:
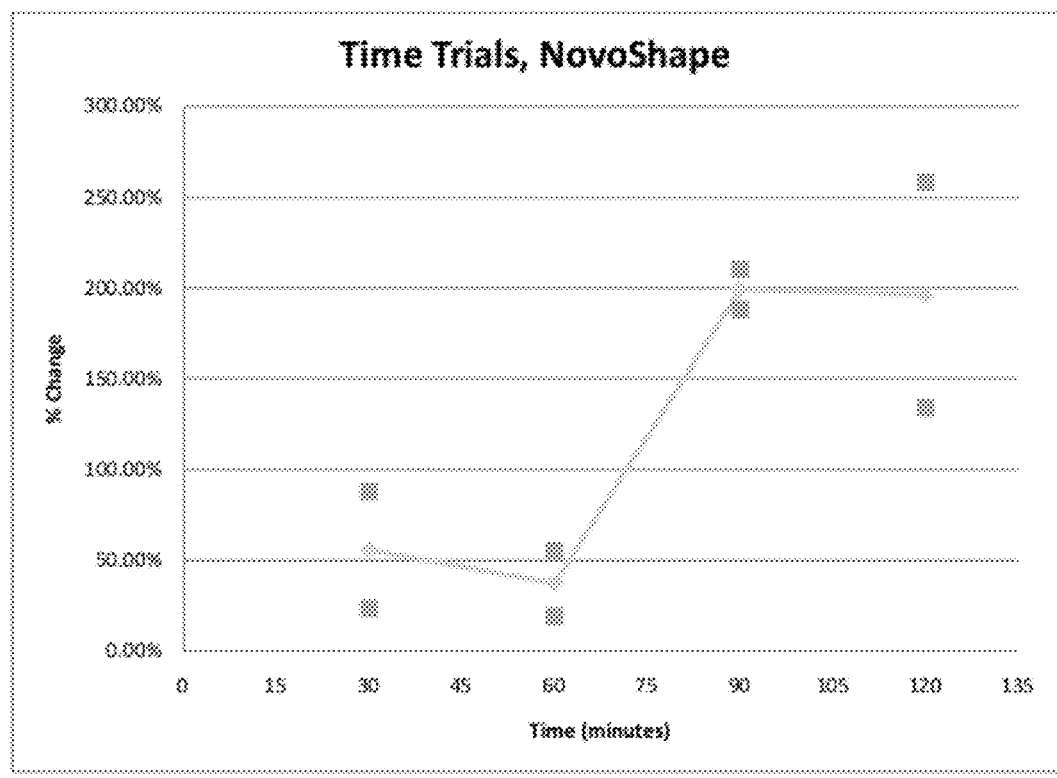
FIG. 9 shows graphing of properties of treated materials according to the present technology.

Two tests were conducted to locate the optimum pH of NovoShape with the pulp solution. The optimum was located approximately at 4.5. Levels outside the range of 3-6 prevent the enzyme from having any effect on the viscosity at all. Temperature Test: FIG. 9

| Temp | initial | after | % change |
|---|---|---|---|
| 20 | 5723 | 4487 | -21.60% |
| 20 | 6353 | 5769 | -10.12% |
| 30 | 7242 | 8114 | 12.04% |
| 30 | 6311 | 7390 | 15.65% |
| 40 | 6147 | 6911 | 12.43% |
| 40 | 5865 | 6345 | 8.18% |
| 50 | 5428 | 9058 | 66.88% |
| 50 | 5372 | 7902 | 47.10% |
| 60 | 5699 | 5901 | 3.54% |
| 60 | 4781 | 5437 | 13.72% |
| 70 | 4607 | 5231 | 13.54% |
| 70 | 4237 | 4637 | 9.44% |

| temp | average |
|---|---|
| 20 | -15.86% |
| 30 | 13.85% |
| 40 | 10.31% |
| 50 | 56.99% |
| 60 | 8.63% |
| 70 | 11.49% |

The average of the two samples was used in the graph. The optimum temperature appears to be 50° C. and outside the range of 40-60° C. the enzyme does not seem to be affective. Time Trials: FIG. 9

| Min | initial | after | % change |
|---|---|---|---|
| 30 | 1884 | 2328 | 23.57% |
| 30 | 2387 | 4487 | 87.98% |
| 60 | 2432 | 2901 | 19.28% |
| 60 | 1644 | 2555 | 55.41% |

-continued

| | | | |
|---|---|---|---|
| 90 | 2060 | 5939 | 188.30% |
| 90 | 1500 | 4655 | 210.33% |
| 120 | 1716 | 6149 | 258.33% |
| 120 | 1884 | 4407 | 133.92% |

| time | average |
|---|---|
| 30 | 55.77% |
| 60 | 37.35% |
| 90 | 199.32% |
| 120 | 196.13% |

There is a correlation between a length of time the sample is placed in a hot water bath to the increase in viscosity. Longer time trials need to be conducted to see where the maximum increase is.

What is claimed:

1. A method of increasing viscosity-increasing effects of an edible refined cellulose fiber comprising:
   providing an aqueous volume;
   adding to the aqueous volume from 0.5% to 20% by weight of edible refined cellulose fiber to form a first reagent composition;
   adding from 0.025% to 8% by volume of pectinase or pectinmethylesterase to the first reagent composition at a temperature of from 20° C. to 80° C.;
   allowing the enzyme to modify the refined cellulose fiber for at least 15 minutes to form a final liquid composition; and
   removing the modified refined cellulose from the final liquid composition;
   and removing liquid from the final liquid composition to produce a viscosity increasing highly refined cellulose mass.

2. The method of claim 1 wherein the refined cellulose is present as from 2% by weight to 8% by weight in the first reagent composition.

3. The method of claim 1 wherein the temperature is maintained between 30° C. and 50° C. for between 30 minutes and three hours before removing the modified refined cellulose.

4. The method of claim 1 wherein the refined cellulose comprises highly refined cellulose having a total dietary fiber (TDF) content greater than 30% as measured by AOAC 991.43 and a water holding capacity greater than five parts water per part fiber as measured by AACC 56-30 and comprises less than 90% soluble fiber.

5. The method of claim 1 wherein pH in the first reagent composition is maintained between 3.0 and 9.0 during conversion to the final liquid composition and the refined cellulose is present as from 2% by weight to 8% by weight in the first reagent composition and the temperature in the first reagent composition is maintained between 30° C. and 65° C.

6. The method of claim 1 wherein after removing the modified refined cellulose from the final liquid composition, the removed modified refined cellulose is dried to form a dry composition.

7. The method of claim 6 wherein the dry composition is a dry refined cellulose composition comprising an enzymatically-modified cellulose fiber or enzymatically-modified refined cellulose particle, the enzymatic modification of the refined cellulose fiber reducing viscosity enhancing properties of the refined cellulose fiber or refined cellulose particle before modification.

8. The method of claim 7 wherein the dry composition comprises a refined cellulose fiber or refined cellulose particle comprises parenchymal cell wall mass selected from the group consisting of citrus pulp, citrus peel, sugar beet pulp, banana pulp, mango pulp, apple pulp or fiber, passion fruit pulp and tomato pulp.

9. The method of claim 7 wherein the refined cellulose fiber or refined cellulose particle comprises orange pulp mass.

10. The method of claim 7 wherein the enzyme used to modify the fiber or refined cellulose particle comprises a pectinase.

11. The method of claim 7 wherein the enzyme used to modify the fiber or refined cellulose particle comprises a pectinmethylesterase.

12. The method of claim 6 wherein the dry composition is a composition comprising an enzymatically-modified fiber or enzymatically-modified refined cellulose particle displaying at least 5% increased viscosity in centipoise as compared to the fiber or refined cellulose particle before modification at a concentration of 3% by weight of fiber to 97% by weight of deionized water at 25° C.±3° C. after 1 minute.

13. The method of claim 12 wherein the dry composition comprises a refined cellulose fiber or refined cellulose particle comprises parenchymal cell wall mass selected from the group consisting of citrus pulp, citrus peel, sugar beet pulp, banana pulp, mango pulp, apple pulp or fiber, passion fruit pulp and tomato pulp.

14. The method of claim 12 wherein the refined cellulose fiber or refined cellulose particle comprises orange pulp mass.

15. The method of claim 12 wherein the enzyme used to modify the fiber or refined cellulose particle comprises a pectinase.

16. The method of claim 12 wherein the enzyme used to modify the fiber or refined cellulose particle comprises a pectinmethylesterase.

17. The method of claim 6 wherein the dry composition comprises a refined cellulose fiber or refined cellulose particle before enzymatic modification that has a total dietary fiber (TDF) content greater than 30% as measured by AOAC 991.43 comprises less than 90% soluble fiber.

18. The method of claim 6 wherein the dry composition comprises a refined cellulose fiber or refined cellulose particle comprises parenchymal cell wall mass, selected from the group consisting of citrus pulp, sugar beet pulp, banana pulp, mango pulp, apple pulp, passion fruit pulp and tomato pulp.

19. The method of claim 6 wherein the enzyme used to modify the fiber or refined cellulose particle comprises a pectinase.

20. The method of claim 6 wherein the enzyme used to modify the fiber or refined cellulose particle comprises a pectinmethylesterase.

* * * * *